US010835179B2

United States Patent
Attal et al.

(10) Patent No.: US 10,835,179 B2
(45) Date of Patent: Nov. 17, 2020

(54) HEADSET FOR BIO-SIGNALS ACQUISITION

(71) Applicant: MYBRAIN TECHNOLOGIES, Paris (FR)

(72) Inventors: Yohan Attal, Paris (FR); Thibaud Dumas, Paris (FR)

(73) Assignee: MYBRAIN TECHNOLOGIES, Paris (FR)

( * ) Notice: Subject to any disclaimer, the term of this patent is extended or adjusted under 35 U.S.C. 154(b) by 498 days.

(21) Appl. No.: 15/533,602

(22) PCT Filed: Dec. 8, 2015

(86) PCT No.: PCT/EP2015/079034
§ 371 (c)(1),
(2) Date: Jun. 6, 2017

(87) PCT Pub. No.: WO2016/091911
PCT Pub. Date: Jun. 16, 2016

(65) Prior Publication Data
US 2017/0332964 A1 Nov. 23, 2017

Related U.S. Application Data

(63) Continuation of application No. 14/563,049, filed on Dec. 8, 2014, now abandoned.

(30) Foreign Application Priority Data

Dec. 8, 2014 (EP) ..................................... 14196835

(51) Int. Cl.
*A61B 5/0478* (2006.01)
*A61B 5/00* (2006.01)
(Continued)

(52) U.S. Cl.
CPC .......... *A61B 5/6803* (2013.01); *A61B 5/0006* (2013.01); *A61B 5/0408* (2013.01);
(Continued)

(58) Field of Classification Search
CPC .... A61B 5/6803; A61B 5/6814; A61B 5/6815
See application file for complete search history.

(56) References Cited

U.S. PATENT DOCUMENTS 4,709,702 A 12/1987 Sherwin
4,967,038 A 10/1990 Gevins et al.
(Continued)

FOREIGN PATENT DOCUMENTS

EP 2368494 A1 9/2011
JP 2001-187034 A 7/2001
(Continued)

OTHER PUBLICATIONS ("Guideline 5: Guidelines for Standard Electrode Position Nomenclature." American Clinical Neurophysiology Society, 2006 (Year: 2006).*
(Continued)

*Primary Examiner* — Niketa I Patel
*Assistant Examiner* — Nathan A Baldwin
(74) *Attorney, Agent, or Firm* — Nixon & Vanderhye

(57) ABSTRACT

Disclosed is an audio-headset for acquisition of a bio-signal from a subject, including a first earpiece; a second earpiece; an arch connecting the first earpiece and the second earpiece; the arch including a hub (4); wherein the arch, the first earpiece and the second earpiece are configured so that the earpieces are placed over a subject's ears when the audio headset is worn by the subject; and at least one posterior branch (1) having a first end extending from the hub and a second free end; the at least one posterior branch (1) including a concave surface with a radius of curvature, a (Continued)

collapsed state when the headset is not worn by the subject and an expanded state when the headset is worn by the subject.

20 Claims, 9 Drawing Sheets

(51) Int. Cl.
    *A61B 5/0496*     (2006.01)
    *A61B 5/0408*     (2006.01)
    *A61B 5/0488*     (2006.01)
    *A61B 5/0492*     (2006.01)
    *A61B 5/0484*     (2006.01)

(52) U.S. Cl.
    CPC .......... *A61B 5/0478* (2013.01); *A61B 5/0488* (2013.01); *A61B 5/0496* (2013.01); *A61B 5/7225* (2013.01); *A61B 5/04085* (2013.01); *A61B 5/0492* (2013.01); *A61B 5/04842* (2013.01); *A61B 5/6815* (2013.01); *A61B 2560/0468* (2013.01)

(56) References Cited

U.S. PATENT DOCUMENTS

| | | | |
|---|---|---|---|
| 5,445,162 A * | 8/1995 | Ives | A61B 5/04004 600/413 |
| 6,154,669 A | 11/2000 | Hunter et al. | |
| 7,761,932 B2 | 7/2010 | Faussett et al. | |
| 8,548,555 B2 | 10/2013 | Jin et al. | |
| 8,655,428 B2 | 2/2014 | Pradeep et al. | |
| 8,706,182 B2 | 4/2014 | Yamashita | |
| 8,731,633 B2 | 5/2014 | Asjes et al. | |
| 2006/0217632 A1* | 9/2006 | Causevic | A61B 5/0482 600/559 |
| 2006/0252978 A1 | 11/2006 | Vesely et al. | |
| 2007/0238945 A1 | 10/2007 | Delic et al. | |
| 2008/0269629 A1* | 10/2008 | Reiner | A61B 5/165 600/544 |
| 2009/0105576 A1 | 4/2009 | Do et al. | |
| 2010/0198042 A1 | 8/2010 | Popescu et al. | |
| 2011/0046503 A1 | 2/2011 | Pradeep et al. | |
| 2012/0143020 A1 | 6/2012 | Bordoley et al. | |
| 2013/0066185 A1 | 3/2013 | Kerth et al. | |
| 2013/0310676 A1 | 11/2013 | Jung | |
| 2014/0051044 A1 | 2/2014 | Badower et al. | |
| 2014/0066740 A1 | 3/2014 | Taranekar et al. | |
| 2015/0182165 A1* | 7/2015 | Miller | A61B 5/6803 600/544 |
| 2015/0230020 A1* | 8/2015 | Jeon | H04R 1/1091 381/74 |
| 2017/0339484 A1* | 11/2017 | Kim | A61B 5/0478 |

FOREIGN PATENT DOCUMENTS

| | | |
|---|---|---|
| JP | 2011-514745 A | 5/2011 |
| WO | 0045701 A1 | 8/2000 |
| WO | 03079897 A2 | 10/2003 |
| WO | 2008109694 A1 | 9/2008 |
| WO | 2008109699 A2 | 9/2008 |
| WO | 2010129026 A2 | 11/2010 |
| WO | 2011/001693 A1 | 1/2011 |
| WO | 2012150528 A1 | 11/2012 |
| WO | 2013126798 A2 | 8/2013 |

OTHER PUBLICATIONS

Valer Jurcak, et al., 10/20, 10/10, and 10/5 systems revisited: Their validity as relative head-surface-based positioning systems, NeuroImage, 2007, pp. 1600-1611, vol. 34, No. 4, Elsevier Inc.

M. Teplan, Fundamentals of EEG measurement, Measurement Science Review, 2002, pp. 1-11, vol. 2, No. 2.

Yu M. Chi, et al., A Practical Mobile Dry EEG System for Human Computer Interfaces, 2013, pp. 649-655, Springer-Verlag Berlin Heidelberg.

* cited by examiner

HEADSET FOR BIO-SIGNALS ACQUISITION

FIELD OF INVENTION

The present invention relates to a set for bio-signals acquisition. The present invention particularly relates to a headset comprising electrodes enabling the acquisition of bio-signals, said headset having a collapsed state and an expanded state wherein the electrodes are in contact with the skin.

BACKGROUND OF INVENTION

Bio-signal is an ultra-fine biomedical signal flowing through the human body. The bio-signal has the shape of current or voltage generated for example from a nerve cell or a muscular cell. The measurement of the bio-signal may be achieved by a surface electrode placed onto the skin and made of a conductor material through which current flows. The group of electro-biological measurement comprises items such as electrocardiography (ECG, heart), electromyography (EMG, muscular contraction), electroencephalography (EEG, brain wave), magnetoencephalography (MEG, brain wave), electrograstrography (EGG, stomach), electrooculography (EOG, eye dipole field). When acquired and transformed into electrical form, bio-signals tend to be described by low voltages, and acquisition of the bio-signals may capture unwanted noise, such as common mode noise (e.g. direct current (DC), offsets from bio-signal detectors, radio frequency interference). Furthermore, biological artifacts can also contaminate acquired bio-signals. The unwanted noise or artifacts can be at a higher voltage than the desired bio-signal, which makes the acquisition process complicated and expensive. Particularly, EEG signals typically range from 10 $\mu V$ to 100 $\mu V$, and can easily be contaminated by the subject's physiological activities for example by any minor movement (eye movement), ECG (pulse), EMG (muscle activation especially biting and blinking), breathing etc.

The EEG recording electrodes are critical for acquiring appropriately high quality data. One of the noise cancelling technique involves conditioning the skin where the electrode must be applied to minimize impedance at the skin interface and to minimize interference. Typically, preparation at the skin interface is invasive including abrasive, depilatory operation, or incisions for scraping skin. Another approach to minimize impedance and interference is to fill the gap between the electrode and the skin interface with a conduction media such as a conductive gel or saline solution. One of the main advantages of gel based electrodes is their robust signal quality, but the main disadvantages are the long montage time and the need to wash the cap and the user's hair after the recording. Therefore, for acquiring bio-signal on the head of a subject, it is appropriate to provide a non-invasive and gel-free electrode guaranteeing the quality of the signal acquisition.

Dry electrodes, using a direct current path between subject's skin to acquire a signal and designed to operate without an explicit electrolyte, are well-known. However, employing dry electrodes in order to acquire a signal from the skin, particularly EEG, is somewhat more challenging in practice due to the high-resistance layer of the skin, presence of hair, and the relative motion of electrodes with respect to the body creating friction movement of electrodes in contact with the body surface. Indeed, dry electrodes which do not have the benefit of a conductive gel are much more sensitive to the condition of the skin and are highly susceptible to motion artifacts, poor electrical conductance due to a very high impedance or any interference sources.

Therefore, there is still a need to provide a technical solution to solve the issue of electrode-skin dry contact for a low-noise, low-artifact bio-signal sensing. For EEG, recording high quality signals reliably through thick layers of hair remains one of the key challenges for enhancing the signal-to-noise ratio.

The use of a headset for positioning electrode on the subjects' head is well-known. For example, U.S. Pat. No. 8,706,182 discloses a headband that can be used for bio-sensing including a plurality of electrodes impregnated with an electrolytic solution. The headset is designed for bringing into contact bio-signal electrodes with site where hair exists. The headset includes an arched shape principal headband extending from the forehead to the parietal and occipital lobes of the subject which comprises occipital and parietal electrodes for measuring EEG. The principal headband holds the headset with its elastic force. The headband also comprises four arms extending from the principal headband, each supporting electrodes: a right and left electro-ocular electrodes designed for being positioned on temples and; a right and a left reference electrodes positioned on earlobes. The electrode includes terminal rod-like members bearing tips, said members being inclined at a certain angle toward the plane on which their tips are positioned for ensuring a contact between the skin and the tips. Contrary to the present invention, this kind of headset does not provide direct contact between the dry electrodes and the skin, as the electrodes do not completely pass through the hair. Moreover, the number and the location of the electrodes are fixed therefore preventing the electrodes to measure other signal than parietal and occipital brain waves. This example also put the emphasis on a problem commonly encountered in the practice of EEG acquisition by means of a headset: it cannot be put instantaneously in the right position instantaneously, in a single move, while maintaining the headset in a stable and comfortable position.

The present invention is designed to avoid the disadvantages of the prior art by providing a headset for measuring bio-signals by means of dry electrodes (i.e. direct skin contact electrodes) for a low-noise, low-artifact bio-signal sensing which can be positioned on a head instantaneously, according to the usual 10-20 and 10-10 systems (Jurcak, Tsuzuki, & Dan, 2007) for scalp locations definition.

SUMMARY

Therefore, the invention relates to a headset comprising flexible branches for suitable positioning dry electrodes in contact with the skin, particularly for bringing into optimal direct contact said bio-signal electrodes with the skin site, even when hair exits on the skin sites. The headset is also configured for preventing undue movement of the electrodes in contact with the skin surface thereby reducing the artifacts. The specific design of the headset enables instantaneous correct positioning of the headset, in a single movement. During this movement, the dry electrodes slide over the head of the subject from the top of the head to its correct location, and passes through the hair. The use of the headset is painless, non-incisive and comfortable. The electrode headset does not cover the entire upper surface of the subject's head, while being sufficiently comfortable and discrete for a use in a clinical or a non-clinical environment. Moreover, said headset enables to choose the location and the number of branches on the skin depending on the requirement.

The present invention relates a headset for acquisition of a bio-signal from a subject, comprising:
  a hub;
  at least 3 flexible branches, each branch having a first end extending from the hub and a second free end, the at least 3 flexible branches defining an opening formed by the relative position of said free ends; and
  at least 3 electrodes, wherein at least one electrode is located on each of the at least 3 flexible branches, said electrodes being configured for acquiring a bio-signal;
wherein the at least 3 flexible branches have a collapsed state; and an expanded state wherein the at least 3 electrodes are in contact with the scalp of said subject; and the headset is expanded from its collapsed state to its expanded state by placing the free ends on the top of head of the subject and progressively lowering and sliding the same with contact to the scalp until the hub is contacted with the top of the head of the subject.

In one embodiment, progressively lowering and sliding the free ends with contact to the scalp ensures constant contact of the electrodes with the scalp.

The present invention relates a headset for bio-signal acquisition comprising:
  a hub;
  at least 3 flexible branches, each branch having a first end extending from the hub and a second free end, the at least 3 flexible branches defining an opening formed by the relative position of said free ends; and
  at least 3 electrodes, wherein at least one electrode is located on each of the at least 3 flexible branches, said electrodes being configured for acquiring a bio-signal;
wherein the at least 3 flexible branches have a collapsed state and an expanded state; and wherein one dimension of the opening in the expanded state is at least 1.5 times higher than said dimension in the collapsed state.

In one embodiment, one dimension of the opening in the expanded state is at least 1.5 times higher than said dimension in the collapsed state. In one embodiment, each flexible branch exhibits an angle between the expanded configuration and the collapsed configuration ranging from 2° to 70°.

In one embodiment, each of the electrodes comprises at least one pin having a first free end comprising a skin contact interface and a second end connected to at least one flexure element. In one embodiment, each of the electrodes comprise at least two pins having a first free end comprising a skin contact interface and a second end connected to at least one flexure element.

In one embodiment, said at least 3 flexible branches are resiliently deformable. In one embodiment, said at least 3 flexible branches are made of a polypropylene or a silicon based material.

In one embodiment, the at least 3 electrodes comprise a ground electrode, a reference electrode, and at least one acquisition electrode. In one embodiment, the at least 3 electrodes comprise at least one dry electrode.

In one embodiment, said at least 3 electrodes are configured to carry out an electroencephalography (EEG), and/or optionally electromyography (EMG), electrooculography (EOG) or electrocardiography (ECG).

In one embodiment, the headset is modular.

In one embodiment, the headset is connected to a bio-signal processor for analyzing and interpreting the measured bio-signal. In one embodiment, the headset further comprises at least one earphone. In one embodiment, the headset comprises an electronic circuit for acquiring a bio-signal comprising an amplifier, an A/D converter and a signal filter. In one embodiment, the headset further comprises a wireless transmitter and/or receiver.

The present invention also relates to a method of providing neurofeedback to at least one subject, the method comprising the following steps:
  placing over the head of a subject an headset for bio-signal acquisition comprising:
    a hub;
    at least 3 flexible branches, each branch having a first end extending from the hub and a second free end, the at least 3 flexible branches defining an opening formed by the relative position of said free ends; and
    at least 3 electrodes, wherein at least one electrode is located on each of the at least 3 flexible branches, said electrodes being configured for acquiring a bio-signal;
  wherein the at least 3 flexible branches have a collapsed state; and an expanded state wherein the at least 3 electrodes are in contact with the scalp of said subject; and
  progressively lowering and sliding the free ends with contact to the scalp until the hub is contacted with the top of the head of the subject;
  acquiring a bio-signal using the headset;
  analyzing the bio-signal; and
  providing a feedback to said subject in accordance with the measured bio-signal.

In one embodiment, analyze of the bio-signal comprises correlating the bio-signal with a specific mental state and providing the subject with a feedback comprising at least one suggestion for improving the subject mental state. In one embodiment, the feedback is a tactile, visual or auditory feedback.

The present invention also relates to an audio-headset for acquisition of a bio-signal from a subject, comprising:
  a first earpiece;
  a second earpiece;
  an arch connecting the first earpiece and the second earpiece; said arch comprising a hub; wherein the arch, the first earpiece and the second earpiece are configured so that the earpieces are placed over a subject's ears when the audio headset is worn by a subject; and
  at least one posterior branch having a first end extending from the hub and a second free end;
  wherein
  the at least one posterior branch comprises at least one electrode configured for acquiring a bio-signal, preferably configured for acquiring a bio-signal at position P3 or P4 in the 10-10 system;
  the at least one posterior branch comprises a concave surface with a radius of curvature, a collapsed state when the audio headset is not worn by a subject and an expanded state when the audio headset is worn by a subject; wherein the ratio between the radius of curvature in the expanded state (CRe) and the radius of curvature in the collapsed state (CRc) is higher than 2.36; and
  the at least one electrode of the at least one posterior branch comprises at least two pins, each pin having a first free end comprising a skin-contact interface and a second end connected to at least one flexure element;
  and wherein
  the first earpiece and the second earpiece comprise each at least one textile electrode, the earpieces and the arch being configured such that the textile electrodes rest against the skin disposed over the mastoid processes when the audio-headset is worn by a subject.

According to one embodiment, the audio-headset comprises at least two posterior branches each having a first end extending from the hub and a second free end; each posterior branch comprising at least one electrode configured for acquiring a bio-signal, preferably the first posterior branch is configured for acquiring a bio-signal at position P3 in the 10-10 system and the second posterior branch is configured for acquiring a bio-signal at position P4 in the 10-10 system; wherein the at least two posterior branches comprise each a concave surface with a radius of curvature, a collapsed state and an expanded state; wherein the ratio between the radius of curvature in the expanded state (CRe) and the radius of curvature in the collapsed state (CRc) is higher than 2.36.

The present invention also relates to an audio-headset for acquisition of a bio-signal from a subject, comprising:
  a first earpiece;
  a second earpiece;
  an arch connecting the first earpiece and the second earpiece; said arch comprising a hub; wherein the arch, the first earpiece and the second earpiece are configured so that the earpieces are placed over a subject's ears when the audio headset is worn by a subject; and
  at least one anterior branch having a first end extending from the hub and a second free end;
  wherein
  the at least one anterior branch comprises at least one electrode configured for acquiring a bio-signal, preferably configured for acquiring a bio-signal at position AF3 or AF4 in the 10-10 system;
  the at least one anterior branch comprises a concave surface with a radius of curvature, a collapsed state when the audio headset is not worn by a subject and an expanded state when the audio headset is worn by a subject; wherein the ratio between the radius of curvature in the expanded state (CRe) and the radius of curvature in the collapsed state (CRc) is higher than 2.10; and
  the at least one electrode of the at least one anterior branch comprises at least two pins, each pin having a first free end comprising a skin-contact interface and a second end connected to at least one flexure element;
  and wherein
  the first earpiece and the second earpiece comprise each at least one textile electrode, the earpieces and the arch being configured such that the textile electrodes rest against the skin disposed over the mastoid processes when the audio-headset is worn by a subject.

According to one embodiment, the audio-headset comprises at least two anterior branches each having a first end extending from the hub and a second free end; each anterior branches comprising at least one electrode configured for acquiring a bio-signal, preferably the first anterior branch is configured for acquiring a bio-signal at position AF3 in the 10-10 system and the second anterior branch is configured for acquiring a bio-signal at position AF4 in the 10-10 system; wherein the at least two anterior branches comprise each a concave surface with a radius of curvature, a collapsed state and an expanded state; wherein the ratio between the radius of curvature in the expanded state (CRe) and the radius of curvature in the collapsed state (CRc) is higher than 2.10.

According to one embodiment, the at least one posterior branch or the at least one anterior branch is releasably connected to the hub.

According to one embodiment, the first earpiece and the second earpiece are circumaural earpieces.

According to one embodiment, the at least one electrode of the first earpiece and the at least one electrode of the second earpieces are fabric electrodes.

According to one embodiment, the at least one electrode of the first earpiece and the at least one electrode of the second earpieces comprises an argent coated textile, preferably an argent coated polyester textile.

According to one embodiment, the at least one electrode of the first earpiece and the at least one electrode of the second earpieces comprise a plurality of contact surfaces.

According to one embodiment, the at least one electrode of the first earpiece and the at least one electrode of the second earpieces comprise a common part from which extends a plurality of strips; and wherein the common part is embedded within the earpiece and at least part of the strips are located on the outer surface of the earpiece.

According to one embodiment, the at least one posterior branch or the at least one anterior branch comprises an amagnetic metal sheet.

According to one embodiment, the at least 3 electrodes (5) of the audio-headset comprise a ground electrode, a reference electrode, and at least one acquisition electrode.

According to one embodiment, the at least 3 electrodes of the audio-headset are configured to carry out an electroencephalography (EEG), and/or optionally electromyography (EMG), electrooculography (EOG) or electrocardiography (ECG).

According to one embodiment, the audio-headset of the invention is further connected to a bio-signal processor for analyzing and interpreting the measured bio-signal.

According to one embodiment, the audio-headset of the invention further comprises an electronic circuit for acquisition of a bio-signal comprising an amplifier, an A/D converter and a signal filter.

According to one embodiment, the audio-headset of the invention further comprises a wireless transmitter and/or receiver.

The present invention also relates to a method for providing neurofeedback to at least one subject, the method comprising the following steps:
  placing on the top of the head of a subject an audio-headset for bio-signal acquisition according to the invention;
  acquiring a bio-signal using the headset;
  analyzing the acquired bio-signal; and
  providing an audio-feedback to said subject in accordance with the measured bio-signal.

According to one embodiment, the analysis of the bio-signal comprises the step of correlating the bio-signal with a specific mental state and providing the subject with a feedback comprising at least one suggestion for improving the subject mental state.

Definitions

In the present invention, the following terms have the following meanings:
  "Acquisition electrode" refers to an active or passive electrode designed for measuring a bio-signal.
  "Active electrode" refers to an electrode comprising at least one amplifier and optionally other electronic components.
  "Branch" refers to an elongated member extending from the hub and having a convex shape designed for imposing a mechanical load (i.e. a pressure) when said branch are in contact with the skin, in situ.

"Collapsed state" or "collapsed configuration" refers to the non-deformed state of the headset wherein the flexible branches are retracted such that the opening formed by the second free ends of the flexible branches is smaller than the opening formed by the second free ends of the flexible branches in the expanded state.

"Contact" or "direct contact" refers to the immediate proximity with the skin of a subject providing a direct current path between an electrode and the subject's body for acquiring a bio-signal.

"Dry electrode" refers to an electrode which does not necessitate the use of an electrolyte (for example a conductive gel) for acquiring a bio-signal, (e.g. an electrode comprising pins spring loaded electrode).

"Expanded state" or "expanded configuration" refers to the state of the headset in use (i.e. in a stable position on the head of the subject), wherein the flexible branches are deformed due to the pressure applied by the flexible branch in contact with the skin.

"Flexure element" refers to an elastic support which is reversibly deformable and configured for supporting and for moving at least one pin along at least an axis. The flexure element enables the distance between the headset and the pin to vary within a certain range determined by the amount of flex permitted by the flexure element. A flexure element is for example a spring, an elastic membrane or any other means known to those skilled in the art.

"Ground electrode" or "bias electrode" refers to an electrode configured to serve as a common reference point for all voltage in the system. In one embodiment, the ground electrode can bias the subject's body to a known reference potential used for the built-in drive amplifier in the hub.

"Load angle" or "angle" refers to the angle between a branch in the expanded configuration and said branch in the collapsed configuration. Said angle corresponds to the deviation of a branch in the expanded state relative to the collapsed state.

"Mental state" refers to a mental condition related to conscious or unconscious brain mechanisms. Said mental state can be measured, for example in order to quantify or model an intellectual, emotional, psychological brain process.

"Modular" refers to the interchangeable design of the headset which is built and organized in self-contained units. Thus, in one embodiment, the headset is configured to allow flexible individual branches, electrodes or pins to be added to the basic headset comprising at least 3 electrodes depending on the requirement. According to one embodiment, the headset is modular for bringing a unit at any location on the head of the subject. The term "modular" may also refer to fact that said individual units can be easily mounted or replaced independently of the other units mounted within the headset.

"Near" (the second free end) means that an element is located on a flexible branch at a short distance from a location, preferably at a distance less than one half of the length of the flexible branch (i.e. the dimension extending from the hub to the free end).

"Opening dimension" refers to a quantitative value defining the size of the opening formed by the second free ends. According to one embodiment, said dimension is a branch span, the circumference of the opening formed by the free ends of the flexible branches or the pitch between two adjacent free ends.

"Pitch" refers to the dimension of the gap between two adjacent free ends of two adjacent flexible branches.

"Passive electrode" refers to an electrode which does not comprise any amplifier.

"Pin" refers to a rod-like or an elongated member comprising a first free end comprising a skin contact interface and a second end connected to at least one flexure element.

"Reference electrode" refers to an electrode to which signals received from another electrode can be compared as a potential difference in order to measure the voltage between the two electrodes.

The terms "Right" and "Left" correspond to the right and the left of a subject when the headset is worn by the subject.

"Subject" refers to an animal, preferably a mammal, more preferably a human. The subject may be a patient, i.e. the subject is awaiting the receipt of, or is receiving medical care or is/will be the object of a medical procedure.

"Span" refers to the dimension of the gap between two opposite flexible branches, from one free end of a flexible ranch, to the opposite free end.

"10-10 system" refers to an internationally recognized method describing the location of scalp electrodes in the context of an EEG test or experiment. The "10" refer to the fact that the actual distances between adjacent electrodes are 10% of the total front-back or right-left distance of the skull. The letters AF, F, T, C, P, TP, CP, PO, FC and O stand for frontal, temporal, central, parietal, and occipital lobes, respectively. Even numbers (e.g. 2, 4, 6, 8) refer to electrode positions on the right hemisphere, whereas odd numbers (e.g. 1, 3, 5, 7) refer to those on the left hemisphere. In addition, the letter codes A, Pg and Fp identifies the earlobes, nasopharyngeal and frontal polar sites respectively.

DETAILED DESCRIPTION

This invention relates a headset for bio-signals acquisition configured for positioning one or more electrodes mounted on the headset within a predetermined target region on a subject's head (based on the 10-10 system). Target region is chosen in accordance with a desired electrode placement scheme (e.g. on parietal and occipital lobes) depending on nature of the measurement. For example, the measurement is several EEG at different locations in order to define a mental state.

According to one embodiment, referring to FIG. 1, the headset for bio-signal acquisition comprises a hub (4); at least 3 flexible branches (1, 2, 3), each branch having a first end (1a, 2a, 3a) extending from the hub (4) and a second free end (1b, 2b, 3b) defining an opening formed by the relative position of said free ends (1b, 2b, 3b). According to one embodiment, the headset also comprises at least 3 electrodes (5), wherein at least one electrode is located on each of the at least 3 flexible branches (1, 2, 3), said electrodes (5) being configured for acquiring a bio-signal.

According to one embodiment, the at least 3 flexible branches (1, 2, 3) of the headset are configured to have reversibly a collapsed state and an expanded state; wherein in the expanded state, the opening is larger than in the collapsed state; wherein in the expanded state, the at least 3 electrodes are in contact with the skin; and wherein after being placed over the head of a subject, the headset reaches the expanded state by progressive lowering the headset until the hub is in contact with the top of the head of the subject.

In the expanded state, the at least three electrodes (5) and the at least three flexible branches (1, 2, 3) maintain the headset in situ.

According to one embodiment, said at least 3 flexible branches (1, 2, 3) are mechanically connected to the hub (4). In one embodiment, the at least 3 flexible branches (1, 2, 3) are reversibly connected. In one other embodiment, the headset is made of a single piece, the hub (4) and the at least 3 flexible branches (1, 2, 3) being integral (i.e. are irreversibly connected). According to one embodiment, the headset made of a single piece is manufactured by molding processes such as compression molding; extrusion molding; injection molding; blow molding; casting; extrusion; 3D printing process, etc.

According to one embodiment, the hub (4) has any form or shape suitable for maintaining said at least 3 flexible branches (1, 2, 3) in a stable position on the top of the head of a subject, for example the hub (4) has a concave diamond shape or a concave triangular shape (as seen in FIGS. 1-7).

According to one embodiment, the headset comprises at least 3, 4, 5, 6, 7, 8, 9, 10, 11, 12, 13, 14, 15, 16, 17 or 18 flexible branches (1, 2, 3). According to one embodiment, each of said branches comprises at least one electrode (5).

According to one embodiment, said at least 3 flexible branches (1, 2, 3) are resiliently deformable.

According to one embodiment, said at least 3 flexible branches (1, 2, 3) are configured for being deformable thereby enabling the opening formed by the second free ends (1b, 2b, 3b) to be modified (e.g. the size and shape of the opening). In one embodiment, the dimension of opening formed by the second free ends (1b, 2b, 3b) may be measured by means of a load angle ($\alpha$, $\beta$), a branch span, a circumference or a pitch between two flexible branches free ends (1b, 2b, 3b). According to one embodiment, the load angle of the headset is ranging from 2 to 70°, or from 5 to 70°, or from 10 to 70°, or from 15 to 70°, or from 20 to 70°, or from 30 to 70°, or from 40 to 70°, or from 50 to 70°, or from 60 to 70°. In one embodiment, the headset in the expanded state has a branch span ranging from 10 cm to 30 cm, or from 12 cm to 20 cm. In one embodiment, the headset in the expanded state has a circumference formed by the free ends of the flexible branches (1b, 2b, 3b) ranging from 30 cm to 70 cm, ranging from 52 cm to 62 cm. In one embodiment, the headset in the expanded state has a pitch from two flexible branches (1, 2, 3) ranging from 5 cm to 20 cm, 5 to 15 cm or 5 to 10 cm.

According to one embodiment, the headset is made of made a polypropylene based material. According to one embodiment, the headset is made of silicon based material. According to one embodiment, the headset is at least partially made of metal, metal alloy, plastic, polymer, composite or a mixture thereof. According to one embodiment, said at least 3 flexible branches (1, 2, 3) are partially made of metals rods. According to one embodiment, the at least 3 flexible branches (1, 2, 3) are made of acrylonitrile butadiene styrene. According to one embodiment, the at least 3 flexible branches (1, 2, 3) are made of polyamide. According to one embodiment, the at least 3 flexible branches (1, 2, 3) are made of an amagnetic metal sheet; said amagnetic metal sheet avoids EEG perturbation. According to one embodiment, the amagnetic metal sheet is at least 0.5 mm thick. According to one embodiment, the amagnetic metal sheet is stamped or molded. According to one embodiment, a rubber part or a foam is connected to the amagnetic metal sheet. According to one embodiment, said rubber part or foam is in contact with the subject's head when the headset is worn to ensure comfort to the subject and thus to improve EEG signal quality by decreasing impedance. According to one embodiment, the foam is thermoformed. According to one embodiment, the foam is made of polyethylene or polyamide. According to one embodiment, the foam or the rubber par comprises at least one casing and the at least one electrode of each branch may be located in the said casing.

According to one embodiment, said material provide to the flexible branches (1, 2, 3) at least enough flexibility to flex in response to the headset positioning on a subject head such that the flexible branches (1, 2, 3) impose a painless pressure on the subject head and maintain the electrodes (5) in contact with the skin. According to one embodiment, aid material provide to the flexible branches (1, 2, 3) at least enough elasticity and flexibility so that the headset can move between an expanded configuration to a collapsed configuration without breaking or without being plastically deformed (i.e. permanently and irreversibly deformed). According to one embodiment, the flexible branches (1, 2, 3) exhibit a shore hardness ranging from 50 to 95 Shores.

According to one embodiment, the headset is made from an isolating material i.e. enabling to isolate the wire connected to the electrodes (5) located inside the headset structure. Advantageously, said isolating material may provide isolation of the bio-signal from environmental interferences. According to one embodiment, the headset structure (i.e. the flexible branches (1, 2, 3) and the hub (4)) encloses electronic wires/channels connected to each at least one electrode (5) located on each flexible branch (1, 2, 3) and conducting the bio-signal. In one embodiment, the headset structure comprises electronic components such as for example an electronic circuit or wireless transmitter/transceiver. This embodiment is advantageous in the case of passive dry electrodes.

According to one embodiment, the pressure imposed by the flexible branches (1, 2, 3) and/or the electrodes (5) to the skin is less than 5N, for example 0.25N, 0.75N, 1N, 2N, 3N, 4N, 5N, or less. According to a one embodiment, the pressure imposed by the headset in contact with the skin may vary, depending on the location on the head and the sensitivity of a subject.

According to one embodiment, a flexible branch (1, 2, 3) has a circular, oval, rectangular, triangular or square section or any geometry which has an ergonomic shape and is designed for guaranteeing the suitable flexibility and the elasticity of the flexible branches (1, 2, 3). For example, the flexible branches (1, 2, 3) may have a section having one or two dimensions (e.g. a diameter, a width, a length) ranging from 1 mm to 1 cm, or from 1 mm to 5 mm.

According to one embodiment, said at least 3 flexible branches (1, 2, 3) consist of a single ramification. According to one other embodiment, the at least 3 flexible branches (1, 2, 3) are made of several ramifications for example at least 2, 3, 4, 5, 6, 7, 8, 9 or 10 ramifications. According to one embodiment, at least one flexible branch comprises several ramifications for example at least 2, 3, 4, 5, 6, 7, 8, 9 or 10 ramifications.

According to one embodiment, a flexible branch (1, 2, 3) has a length (i.e. the dimension of the flexible branch (1, 2, 3) extending from the hub (4) to the free end (1b, 2b, 3b)) ranging from 1 cm to 30 cm, or 10 cm to 15 cm. According to one embodiment, the at least flexible branch (1, 2, 3) have different length depending on the part of the head to be reached, the size and the shape of the skull of the subject. The at least 3 flexible branches (1, 2, 3) may have different size and shape depending the bio signal to be measured. For example the size and the shape depend on the subject morphology, the area that is suitable to reach for measuring a bio-signal (e.g. an EEG, an ECG) at a desired location while ensuring a stable position of the headset on the subject's head. According to one embodiment, said at least three flexible branches (1, 2, 3) have a length which is configured to be bended due to the elastic properties of the material.

According to one embodiment, said at least 3 flexible branches (1, 2, 3) are telescopic i.e. extensible or compressible by the sliding of overlapping sections. According to one embodiment, the flexible branches (1, 2, 3) has a variable length which can be adjusted (i.e. may be shortened or lengthened) depending on the requirement.

Advantageously, the at least 3 flexible branches (1, 2, 3) are designed for being adaptable to any size and shape of a subject. Indeed, each individual has a unique morphology; particularly a unique skull shape. Said flexible branches (1, 2, 3) are adaptable to any skull by providing at least 3 contacts points in contact with the skin, located on the free ends (1b, 2b, 3b) of the flexible branches (1, 2, 3). Moreover, the flexibility and the reduced number of branches improve the adaptability of the headset to any kind of skull morphology.

According to one embodiment, the headset for acquisition of a bio-signal from a subject comprises:
- a hub (4);
- at least 3 flexible branches (1, 2, 3), each branch having a first end (1a, 2a, 3a) extending from the hub (4) and a second free end (1b, 2b, 3b); and
- at least 3 electrodes (5), wherein each flexible branch (1, 2, 3) comprises at least one electrode (5), said electrodes (5) being configured for acquiring a bio-signal;

wherein the first flexible branch (1) comprises a concave surface with a radius of curvature, a collapsed state when the headset is not worn by a subject and an expanded state when the headset is worn by a subject.

According to one embodiment, the radius of curvature in the collapsed state (CRc) and the radius of curvature in the expanded state (CRe) is such that:

$$CRc = \frac{CRe}{\Delta};$$

wherein $\Delta$ is equal to at least twice the standard deviation of the curvature radius of the scalp at a given position in the 10-10 system.

According to one embodiment, the second branch (2) and the third branch (3) are joined and form an arch. According to one embodiment, the said arch is stamped or molded. According to one embodiment, the hub is connected (e.g. screwed) to the arch between the second and the third branches (2, 3) (i.e. on the top of the arch).

According to one embodiment, the headset comprises a plurality of flexible branches comprising a concave surface with a radius of curvature, a collapsed state and an expanded state. According to one embodiment, each of said branches is connected to the arch.

According to one embodiment, the second and third branches (2, 3) form an arch and the first branch (1) is removable from the arch. According to one embodiment, the headset comprises a plurality of removable branches. According to one embodiment, each branch which may be removed from the arch comprises a concave surface with a radius of curvature, a collapsed state and an expanded state.

According to one embodiment, the headset comprises at least 3, 4, 5, 6, 7, 8, 9, 10, 11, 12, 13, 14, 15, 16, 17 or 18 flexible branches (1, 4) comprising a concave surface with a radius of curvature, a collapsed state and an expanded state.

According to one embodiment, the headset comprises at least 3 electrodes (5), at least one electrode (5) is located on each of the at least 3 flexible branches (1, 2, 3). The at least three electrodes are configured for acquiring bio-signals.

According to one embodiment, the at least three electrodes (5) are positioned on the internal surface of the headset (i.e. the hub (4) or the flexible branches (1, 2, 3)). According to one embodiment, the at least three electrodes (5) are located on the internal surface near the second free end (1b, 2b, 3b) of the flexible branches (1, 2, 3). In one embodiment, the at least three electrodes (5) are located at the end of a flexible branch (1, 2, 3). According to one embodiment, the at least three electrodes (5) are positioned at any location along the internal surface of the headset.

Advantageously, the at least one electrode (5) located at the end of each flexible branch (1, 2, 3) improves the pressure applied on the electrodes in contact with the skin of the subject, in situ. Consequently, said at least three electrodes (5) also improve the secured positioning of the headset on a subject's head.

According to one embodiment, said at least 3 electrodes (5) comprise a ground electrode, a reference electrode and at least one acquisition electrode.

Bio-signal records are bipolar i.e. they represent the difference in potential between the acquisition electrode of interest, and a reference electrode. In one embodiment the reference and ground electrodes are placed on the skin to measure brain signal compare to another brain signal as reference. Biological activity (such as brain activity) but also environmental electric and magnetic fields may generate skin difference in potential. Therefore, according to one embodiment, the headset of the invention also includes a ground electrode which isolates a human subject from the ground of the power supply. This configuration comprising a ground, a reference and an acquisition electrode is designed to reject the spatially constant common-mode potential and amplify the difference in potential between pairs of skin locations such that the output voltage is proportional to skin difference in potential difference generated within the body. Impedances for all acquisition electrodes are compared to both the ground and the reference electrode during data processing.

According to one embodiment, the headset includes at least one ground electrode and at least one reference electrode. In some embodiment, both reference and ground electrodes are configured for being located behind the ears, on the mastoids. According to one embodiment, acquisition electrodes are placed on area where skin voltage is changing and reference electrode on a neutral site i.e. an area where the skin voltage vary as little as possible. According to one embodiment, the headset is configured such that the reference electrode is placed on the mastoids, vertex, ear lobes (particularly ipsilateral-ear, contralateral ear), non-cephalic area or on the tip of the nose. According to another embodiment, the reference is calculated by averaging the signal of several acquisition electrodes. According to one embodiment, the reference electrode is located on the right side mastoid. According to one embodiment, the reference electrode is located on the left side mastoid. Mastoids are two ideal locations to measures non-brain potentials with a minimal amount of artifacts.

According to one embodiment, the headset is configured such that the ground electrode is placed on the forehead of the subject. In some embodiment, reference electrode is located at any location on a subject head. According to one embodiment, the headset is configured such that the ground electrode is placed on ear location of the subject. According to one embodiment, said ground electrode is located on left side mastoid. According to one embodiment, said ground electrode is located on right side mastoid.

According to one embodiment, the headset also includes at least one electrode (5) placed on the frontal lobe. In one embodiment, two electrodes (5) respectively located on the right and on the left hemisphere; and at least one electrode (5) placed on the parietal lobe. In one embodiment, two electrodes (5) respectively located on the right and on the left hemisphere. According to one embodiment, the headset comprises several acquisition electrodes, for example 1, 4, 5, 8, 10, 16, 20, 25, 30, 40, or 50 acquisition electrodes. In one embodiment, the headset may comprise an equal number of acquisition and reference electrodes, an equal number of acquisition and ground electrodes and/or an equal number of both acquisition, ground and reference electrodes.

Advantageously, said ground electrode enables to improve and optimize noise reduction in the amplifier, particularly common mode rejection. A ground electrode is needed to serve as a common reference point for all voltage in the system.

According to one embodiment, each flexible branch (1, 2, 3) comprises at least one electrode (5). According to one embodiment, each flexible branch (1, 2, 3) comprises 1, 2, 3, 4 or 5 electrodes (5).

According to one embodiment, said at least 3 electrodes (5) comprise at least one dry electrode. According to one embodiment, the at least 3 electrodes (5) are active electrodes. According to one embodiment, the at least 3 electrodes (5) are passive electrodes. According to one embodiment, at least one acquisition electrode is a dry electrode. According to one embodiment, the ground and/or the reference electrodes are passive electrodes. According to one embodiment, all the acquisition electrodes are dry passive electrodes (i.e. dry electrodes which have no inbuilt circuitry). According to a one embodiment, reference and ground electrodes are dry active electrodes (i.e. dry electrodes which have an inbuilt circuitry). In some embodiment, the ground or/and reference electrodes comprises an adherent substance or a conductive substance. In some embodiment, all the electrodes (5) located on an area where hair exists are dry electrodes.

According to one embodiment, the active electrode comprises at least one amplifier, said amplifier having a gain ranging from 1 to 5000 or from 1 to 2500, or from 1 to 1000, or from 1 to 500. According to one embodiment, the active electrode comprises an impedance converter. According to one embodiment, the active electrode comprises an amplifier and set of protections such as Transient Voltage Suppression (TVS) diodes and signal frequency filters for example.

According to one embodiment, the active electrode comprises an amplifier which has a low intrinsic noise (<76 nV P-P) in the frequency range of 0.1 to 10 Hz for example. The amplifier may have a low drift and low offset voltage. This configuration enables to provide the best separation of bio-signal from interference signals and noise. In some embodiment, the amplifier has a high common mode rejection ratio for example at least 110 dB.

According to one embodiment, the at least three electrodes (5) are electrically connected to an electronic circuit (13) that is configured to receive and processing a raw signal from the electrodes (5) and to provide an output signal. According to one embodiment, electronic circuit (13) is mounted or house within an active electrode, preferably in acquisition electrodes. According to one embodiment, electronic circuit (13) is mounted or house within at least one active electrode.

According to one embodiment, said at least 3 electrodes (5) are configured to carry out an electroencephalography (EEG) and/or optionally electromyography (EMG), electrooculography (EOG) or electrocardiography (ECG).

In some embodiment, at least 2 acquisition electrodes are configured to carry out an EEG, and optional acquisition electrodes are configured for measuring muscular, cardiac, ocular activity for correlating bio-signals to a mental state, or for improving the signal acquisition by discriminating different physiological artifacts from the skin voltage.

According to one embodiment, each of the at least 3 electrodes (5) comprise at least 1 pin (6), said at least one pin (6) being connected to at least one flexure element (7) at one first end and comprising a skin contact interface (8) on a second end. According to one embodiment, the reference, ground and acquisition electrodes comprise at least one pin (6). According to one embodiment, the acquisition electrodes comprise at least one pin (6). According to one embodiment, the electrode of the first branch (1) comprises at least 1 pin (6), said at least one pin (6) being connected to at least one flexure element (7) at one first end and comprising a skin contact interface (8) on a second end. According to one embodiment, the electrode of each branch which is plugged to the arch comprises at least 1 pin (6), said at least one pin (6) being connected to at least one flexure element (7) at one first end and comprising a skin contact interface (8) on a second end.

According to one embodiment, said pins (6) located in contact with the subject's skin form a skin contact interface (8). According to one embodiment, the pins (6) are configured for passing across the hairs while ensuring a conductive contact. In one embodiment, only the acquisition electrode comprises at least two pins (6), said acquisition electrode being located on the head of the subject. In one embodiment, the electrode comprises at least 1, 2, 4, 8, 16, 20, 24, 28, 32 or 50 pins (6). In one embodiment, pins are rod-like members having a diameter ranging from 0.25 mm to 1 cm, or from 1 to 2 mm. In one embodiment, the pins (6) are made in a conductive material forming elongated protrusions. According to one embodiment, said elongated protrusions have any shape providing sufficient and painless contact with the subject skin through the hair, for example a cylindrical, triangular or rectangular shape with a rounded free end forming the skin contact interface (8). According to one embodiment, the ground and/or reference electrodes which are not located on an area where hair exists comprise only one single skin contact interface (8) with the skin of the subject.

According to one embodiment, a pin imposes a pressure applied by the pin in contact with the skin which is less than 5N, for example 0.25N, 0.75N, 1N, 2N, 3N, 4N, 5N or less.

According to one other embodiment, the length of the pin (6) can be variable and length is ranging from 1 mm to 20 mm, or 4.5 to 7.5 mm. Advantageously, the variability of the length enables to choose the optimal length depending on the head location, the hair length and density and more generally, depending on the subject morphology.

According to one embodiment, said at least 3 electrodes (5) comprise at least 2 pins (6), each of said at least two pins (6) being connected to at least one flexure element (7) at one first end and comprising a skin contact interface (8) on a second end. According to one embodiment, the at least 2 pins are arranged electrically in parallel. According to one embodiment, the electrode of the first branch (1) comprises at least 2 pins (6), each of said at least two pins (6) being connected to at least one flexure element (7) at one first end and comprising a skin contact interface (8) on a second end. According to one embodiment, the at least 2 pins are arranged electrically in parallel. According to one embodiment, the electrode of each branch which is plugged to the arch comprises at least 2 pins (6), each of said at least two pins (6) being connected to at least one flexure element (7) at one first end and comprising a skin contact interface (8) on a second end. According to one embodiment, the at least 2 pins are arranged electrically in parallel.

Advantageously, the electrically parallel configuration enables to decrease the contact impedance while acquiring easily much more head points across the hairs. The use of active electrodes also contributes to reduce the contact impedance.

In one embodiment, dimensions of the pins (6) and material are configured to provide contact impedance ranging from 152 to 300 kn. This impedance will decrease with the number of pins and their electrically parallel connection, regardless of the nature of the electrode (i.e. active or passive). Moreover, active electrode drastically decreased impedance by using an amplifier as impedance converter which further decreases said impedance. Indeed, the contact impedance of non-dry electrode is about 5 k$\Omega$ rather than the contact impedance of a dry electrode could increase until about 500 k$\Omega$. In order to provide an acquisition system comprising dry electrodes enabling to perform a bio-signal acquisition with a quality comparable to a non-dry system, it is particularly important to reduce said contact impedance.

According to one embodiment, the contact pattern of at least one electrode (5) in contact with the skin is variable by means of a matrix setting (10). A matrix setting (10) is an electrode housing imposing a specific pattern of pins (6) which enables the pins (6) to be easily and independently mounted on the headset.

According to one embodiment, the pins (6) are made in a material which is water-impermeable, durable and biocompatible for skin contact. In one embodiment, said pins (6) are mounted on a matrix setting (10) imposing a pattern with a number of pins connections and a predetermined distance between two pins. Said pins (6) are reversibly connected to the matrix setting (10), independently from other pins (6). In one embodiment, the pins (6) are reversibly plugged on the matrix setting (10). According to one embodiment, the distance between two pins (6) is ranging from 0.25 mm to 10 mm, or 2 mm to 3 mm. According to one embodiment, the pins (6) in contact with the skin are made of and optionally coated with a conductive material.

According to one embodiment, the skin contact interface (8) is made of gold. According to one embodiment, the pin (6) is connected to an electronic interface (9) comprising an electronic circuit (13) such as CMS. According to one embodiment, the end of the pin in contact/connected to the electronic interface (9) is made of Nickel-Gold. In one embodiment, the surface quality of the skin contact interface (8) is configured to be soft or smooth to improve the comfort of the headset. Advantageously, the pins (6) can make direct contact with the subject's skin by means of its protruding structure which can easily pass through the hair.

In some embodiment, reference, ground and acquisition electrodes, more particularly pins (6), are individually connected to an individual flexure element (7). According to one embodiment, both pins (6) are connected to a common flexure element (7). According to an embodiment, the flexure element (7) is made in a conductive material. For example, a flexure element (7) may be a metallic spring loaded on a pin or a flexible conductive membrane. According to one embodiment, reference, ground and acquisition electrodes are spring-loaded. According to an alternative embodiment, only acquisition electrodes are spring-loaded. Advantageously, the flexure element (7) increases the adaptation to the shape of the skin and allows the pressure imposed by the pins (6) in contact with the skin to be controlled and painless. Said flexure element (7) pushes the pins (6) through the strands of hair and maintains a constant painless pressure imposed by the pins (6) in contact with the skin, for all positions. The flexure element (7) also allows the distance from the contact element (i.e. the free end (8) or the pin (6)) to vary within a certain range determined by the amount of flex permitted by the flexure element (7) and the flexible branches (1, 2, 3). For example the distance from the skin interface (8) and circuit contact interface (9) ranges from 1 mm to 5 mm, or 3 mm to 4 mm. Finally, the use of pins (6) loaded on a flexure element (7) improves the secured positioning of the headset on the subject's head, particularly when the pins (6) are located at the free end (1*b*, 2*b*, 3*b*) of the flexible branches (1, 2, 3). Indeed, the pins (6) provide an additional support on the subject skin.

According to one embodiment, referring to FIG. 8, at least one electrode (5) of the headset is made of 3 pins (6) loaded on a spring (7). The upper free end (8) of the pin (6) is intended to be in contact with the skin's subject and thereby forming a skin contact interface (8). The assembly of said pin (6) and spring (7) are plugged on a matrix setting (10). The lower end of the spring (7) is connected to a surface mounted device (CMS) and forms an electronic interface (9) allowing an electronic connection between a pin (6) and an electronic circuit (13) for processing the bio-signal.

In one embodiment, each electrode (5) comprises at least one contact element (for example a pin, a protrusion member, a plate) in contact with the skin of a subject and designed for conducting a current and optionally said contact element is connected to a sensor circuitry. In some embodiment, the acquisition electrode for measuring a bio-signal is a resistive electrode having a direct contact with the skin of the subject with direct current path between the subject's skin and the contact/interface element. In another embodiment, the electrodes are capacitive electrodes without contact with the skin but having a capacitive link between the skin and the electrode, for example the electrode is made in a highly dielectric material.

According to one embodiment, the headset is designed for clinical or non-clinical application. Advantageously, the headset is designed to be quickly positioned without the assistance of a trained technician and is also discrete and comfortable for an ambulatory use.

According to one embodiment, the headset has an expanded configuration in situ (i.e. lowered on the subject head) corresponding to a deformed state of the flexible branches (1, 2, 3). According to one embodiment, the opening dimension of the headset in the expanded state is at least 1.5; 2; 2.5; 3; 3.5; 4; 4.5; 5; 6; 7; 8; 9 or 10 times higher than said dimension in the collapsed state. According to one embodiment, said opening dimension is the branch span, the circumference of the opening formed by the free ends of the flexible branches (1*b*, 2*b*, 3*b*) or the pitch between two adjacent free ends (1*b*, 2*b*, 3*b*).

According to one embodiment, each of the flexible branch (1, 2, 3) in the expanded state exhibits an angle ($\alpha$, $\beta$) between the expanded configuration and the collapsed configuration ranging from 2° to 70°, or from 5 to 70°, or from 10 to 70°, or from 15 to 70°, or from 30 to 70°, or from 50 to 70°.

FIG. 2 illustrates the deformability of the headset, particularly the variation of its shape/size between the collapsed to the expanded configurations. According to one embodiment, referring to FIG. 2, the headset is illustrated with the flexible branches in the expanded configuration (1, 2) and in the collapsed configuration (1', 2'). The position of the flexible branch in the expanded state (1, 2) and the position of the flexible branch in the collapsed state (1', 2') form load angles (α, β). The first load angle (α) relative to the flexibility of a first flexible branch (1, 1') is substantially equal to 40°. The second load angle (β) relative to the flexibility of a second flexible branch (2, 2') is substantially equal to 15°. According to one embodiment, the load angles (α, β) are equal or different. According to one embodiment, the value of the load angles (α, β) depends on the mechanical properties of the flexible branches (1, 2, 3) (e.g. the flexibility, the elasticity . . . ).

According to one embodiment, the headset has a collapsed configuration when not using (i.e. before or after use) corresponding to a non-deformed state of the flexible branches (1, 2, 3). According to one embodiment, in the collapsed state, said opening is smaller than the size of the subject head. Advantageously, the flexible branches (1, 2, 3) are reversibly deformable for being adaptable to any kind of morphology, size and particularly shape of the subject head. Indeed, the deformability of the headset and the reduced number of flexible branches (1, 2, 3) allow the headset to be adaptable to a large range of skull morphology unique to each individual, contrary to classic headset for EEG recording.

According to one embodiment, the headset, initially in a collapsed state, is designed for being lowered onto the head, preferably by using the branches (1, 2, 3) for positioning and pushing the headset. The lowering movement refers to a pushing movement of the headset, the opening formed by the second free ends (1b, 2b, 3b) being positioned on the upper surface of the subject. During said lowering movement, the subject head applies a pressure against the flexible branches (1, 2, 3) thereby progressively deforming them and enlarging the opening formed by said free ends (1b, 2b, 3b) of the headset. The headset is also designed for being removed from the subject head by only pulling the headset, preferably by means of the flexible branches (1, 2, 3), thus progressively retracting said opening thereby switching back the headset in a collapsed state. The headset is maintained in a secured position by means of contact points in contact with the subject's skin. In one embodiment, said contact points are located at the free ends (1b, 2b, 3b) of the flexible branches (1, 2, 3). In one embodiment, said contacts points comprise the electrodes (5) which are pressed against the subject's skin. According to one embodiment, said contact point is a pin (6). According to one embodiment, said contact point is not an electrode (5) or a pin (6). According to one embodiment, the headset is maintained in a secured position by means of the at least three electrodes (5) located at the free ends of the at least 3 flexible branches (1b, 2, 3b).

Advantageously, the expanded configuration is designed for suiting different morphologies, sizes and shapes of the head while ensuring a stable positioning of the headset. Advantageously, said configurations of the headset allow the headset to be folded into the collapsed state for an easy storage. It also allows the headset to be quickly and suitably positioned on the subject's head.

According to one embodiment, referring to FIG. 3, an implementation of the headset disclosed on FIG. 4 in situ is shown. The terms "left" and "right" refers the right and the left of the subject wearing the headset. In this embodiment, the headset is positioned onto a subject head in an expanded state. The headset includes right and left flexible branches (1r, 1l) wherein the free ends of the flexible branches (1rb, 1lb) are positioned on the parietal lobe. Said right and left branches (1r and 1l) include acquisition electrodes for acquiring a bio-signal (e.g. an EEG). In one embodiment, the at least 3 electrodes (5) are located near the second free ends of the flexible branches (1rb, 1lb), in contact with the skin of the subject. The headset is configured for measuring brain activity of the parietal lobe area. More specifically, in one embodiment, both measured positions are P3 and P4, respectively on the left and right parietal lobes, referring to the 10-10 system. The headset also comprises peripheral right and left branches (2 and 3) extending from the hub (4) positioned over the head of the subject: the right branch (3) extends on the right side of the head directly behind the ear on the mastoid. The left branch (2) extends on the left side of the head directly behind the ear on the mastoid. Mastoids are two ideal locations to measures non-brain potentials with a minimal amount of artifacts. This configuration enables to prevent movement of the headset on the head of the patient, the headset being blocked by means of the peripheral branches (2, 3). Said peripheral branches (2, 3) include respectively a ground and a reference electrodes, and are located on the second free ends (2b, 3b) of the peripheral branches (2, 3), in contact with the skin of the subject.

According to one embodiment, referring to FIG. 6, an implementation of the headset disclosed on FIG. 5 in situ is shown. In this embodiment, the headset is positioned onto a subject head in an expanded state. The headset includes right and left branches (1r and 1l) wherein the free ends are positioned on the frontal area. More specifically, in one embodiment, both measured positions are AF3 and AF4, respectively on the left and right frontal lobes, referring to the 10-10 system. Said right and left flexible branches (1ra and 1rb) include acquisition electrodes for acquiring a bio-signal. The at least 3 electrodes (5) are located near the free ends of the flexible branches (1lb, 1rb), in contact with the skin of the subject. The headset is configured for measuring brain activity of the frontal lobe area. The headset also comprises peripheral right and left branches (3 and 2, not shown on FIG. 4) extending from the hub (4) positioned over the head of the subject.

According to one embodiment, referring to FIG. 7, an implementation of the headset is disclosed. In this embodiment, the headset includes peripheral right and left branches (2, 3) extending from the hub (4) positioned over the head of the subject. The headset further includes two anterior right and left flexible branches (11r, 11l) wherein the free ends are positioned on the frontal lobe area; and two posterior right and left branches (12r, 12l) wherein the free ends are positioned on the parietal lobe area.

According to one embodiment, the headset is modular. According to one embodiment, the headset is configured for being modular by adding at least one flexible branch (1, 2, 3) to the hub (4), and/or adding at least one electrode (5) to a flexible branch (1, 2, 3), and/or adding a pin (6) to an electrode (5). In this embodiment, electrodes (5) are modular units i.e. the electrodes (5) are configured for allowing individual electrodes (5) to be easily mounted or replaced independently of the other electrodes (5) mounted on the headset. According to another embodiment, the flexible branches (1, 2, 3) are modular units i.e. the flexible branches (1, 2, 3) are configured to be easily mounted or replaced on the headset, for example by connecting/disconnecting said flexible branches (1, 2, 3) to the hub (4) depending on requirement. In some embodiment, the electrodes (5) are themselves made of individual units (e.g. pins (6) or conductive plate or the electronic component included into the electrode) which are modular i.e. which can be easily mounted or replaced. In some other embodiment, other modular units such as electronic components (wireless transmitter, earphone, amplifier, wires) may be added to the headset in order to customize the headset depending on requirement (for example kind of mental state which is intended to be detected with the headset or the need to impose a neurofeedback to the subject). In one embodiment, one or more modular units (e.g. flexible branch (1, 2, 3), electrode (5), earphone, electronic component) can be added to the headset independently to each other depending on requirement or application of the bio-signal acquisition. In one embodiment, the flexible branches (1, 2, 3) are mounted according to a desired electrode placement scheme relative to the subject head. For example electrodes (5) located on the flexible branches (1, 2, 3) are placed on frontal, central, temporal, parietal and/or occipital area.

Advantageously, the modularity of the headset enables to easily adapt the number of flexible branches (1, 2, 3) and/or electrodes (5) depending of the application, the subject morphology or the cost of the headset. It also enables to quickly replace any defective item in the headset.

According to one embodiment, the second and third branches (2, 3) form an arch and the first branch (1) is removably connected from the said arch. According to one embodiment, the headset comprises a plurality of removable branches. According to one embodiment, the branches are connected to the hub by means of a plug. According to one embodiment, the plug offers a mechanical resistance of at least 15N. According to one embodiment, the headset comprises a first plug facing the front of the headset and a second plug facing the back of the headset. According to one embodiment, the plug is based on the elastic deformation of the branches. According to one embodiment, as depicted in FIG. 15, the audio-headset (16) comprises an arch (15) and a hub (4). The branches (1l, 1r) are removably connected to the hub by means of a plug. In particular, the branches (1l, 1r) comprise elastic blades (17) which may be deformed to secure the branches to the hub (4). Once put into the hub (4) the said elastic blades (17) fit into a recess. To unplug the branches, one needs to apply a force in order to elastically deform the blades (17). According to one embodiment, each branches connected to the arch comprises at least one elastic blade (17). According to one embodiment, said elastic blade (17) is made of acrylonitrile butadiene styrene. According to one embodiment, when the branches are plugged to the hub, electrical connection between the branches and the hub is ensured.

An exemplary embodiment of the electronic devices integrated in the headset is illustrated in FIG. 9. Electrodes (5) are located on the subject's head and acquired an analogical signal. Said signal is sent to the electronic circuit (13) located inside the headset. Said electronic circuit (13) is also connected to an external processor, for example an external device (smartphone or cloud). Referring to FIG. 9, according to one exemplary embodiment, the electronic circuit (13) comprises at least one of the following functional parts:
 an A/D interface;
 a signal processing part;
 a power supply;
 a wire communication part and/or a wireless communication part; and
 a micro-controller unit (MCU).

According to one embodiment, the A/D interface is designed for digitized the analogical signal. According to one embodiment, the A/D interface comprises a signal input multiplexer and/or comprises a programmable gain amplifier and/or comprises a means for impedance measurement. For example, the A/D interface comprises an input signal amplifier, a programmable gain amplifier, an analog to digital converter and/or an impedance measurement. According to one embodiment, the hub (4) comprises an Analogical to Digital (A/D) converter. In some embodiment, said A/D converter after amplification coded with a resolution of 24 bits has a Signal to Noise Ratio (SNR) of 120 dB per channel.

According to one embodiment, the signal processing part is designed for pre-treating the signal (i.e. before sending the signal to a processor for analysis). According to one embodiment, the signal processing is configured for analyzing the signal. An exemplary pre-processing algorithm comprises measuring the quality of the acquisition, imposing digital filter and/or encoding/crypting data.

According to one embodiment, the wire or a wireless communication parts are designed for transmitting the signal to an external entity, for example a smartphone. According to one embodiment, said external device is designed for processing the bio-signal for example, for analyzing the EEG and interpreting the mental state of the subject wearing the headset. According to one embodiment, the headset includes wire communication links (for example by means of an USB communication) suitable for installing a firmware, exporting stored data or even charge a power supply for example a battery.

According to one embodiment, a Micro-Controller Unit (MCU) is designed for controlling all or a part of the functional parts connected to the MCU. According to one embodiment, said MCU is connected for sending and receiving data from a means for pre-processing an algorithm and a wireless communication means.

According to one embodiment, the electronic circuit (13) architecture is integrated in one of the at least 3 flexible branches (1, 2, 3) of the headset or integrated to the hub (4).

According to one embodiment, said headset includes an electronic circuit (13) for acquiring a bio-signal comprising an amplifier, an A/D converter and optionally a signal filter.

According to one embodiment, the electronic circuit (13) comprises a signal amplifier. The signal needs to be amplified to make it compatible with devices such as displays, recorders or A/D converters. According to one embodiment, the amplifier is selected in order to provide amplification selective to the physiological signal, for example EEG signal and rejected superimposed noises for both patients and electronic components of the electrodes (5). According to one embodiment, the headset comprises an impedance converter comprising an amplifier.

According to one embodiment, said electronic circuit (13) comprises a low-pass signal filter. According to one embodiment, the low-pass filter is in the order 1 to 8. Advantageously, the low-pass filter is configured to protect bio-signals from non-bio-signals such as environmental interferences. According to one embodiment, the amplification is based on impedance conversion (i.e. to pass from a high to low impedance) using an amplifier, preferably an ultra-low noise amplifier, of gain equal to 1. According to one other embodiment, the amplification is based on signal amplification with higher gain values with a configuration enabling a gain at least equal 2, for example a gain of 10, 20, 30, 40, 50, 100 for classical programmable gain amplifier or 1000, 5000 or $10^6$ in the case of high gain amplifier.

Advantageously, the amplification allows the quality of the bio-signal acquisition to be improved and readable. In some embodiment, the electronic circuit (13) comprises a high-pass filter for reducing low frequencies coming from bio-electric flowing potentials (e.g. breathing, cardiac activity . . . ), for example with a cut-off frequency ranging from 0.1 to 2 Hz, or 0.1 to 0.7 Hz, or equal to 0.4 Hz.

According to one embodiment, the hub (4) comprises an amplifier montage comprising by one or more amplifier. In some embodiment, said amplifier has a gain ranging from 2 to 5000, or ranging from 2 to 2500, or from 2 to 1000, or to 2 to 50. According to one embodiment, the hub (4) comprises an impedance converter. According to one embodiment, the hub (4) comprises an amplifier which has a very low input-referred noise about 1 µV (70 Hz-BW) and low intrinsic noise (<76 nV P-P) in the frequency range of 0.1 to 10 Hz for example. The amplifier may have a low drift and low offset voltage.

According to one embodiment, said electronic circuit (13) comprises a protection. According to one embodiment, the protection includes at least one diode for circuit protection, for example a diode with low leakage current to protect from voltage spikes and/or double diodes with low leakage. According to one embodiment, the protection also includes at least one resistance, for protection from current variability. According to a preferred embodiment, the value of the resistance is displayed in a range from 500Ω to 1 MΩ, for example 500 to 0.5 MΩ, even 1 KΩ. Advantageously, the protection acts as a shield of the input, especially in case of the absence of an amplifier to convert impedance.

Advantageously, said electronic circuit (13) amplifies the biomedical signal to a treatable level for a more precise and easier measurement of the signal, especially EEG wherein the level of signal is excessively fine (i.e. several tens of microvolts).

According to one embodiment, the headset is further connected to a bio-signal processor for analyzing and interpreting the measured bio-signal. According to one embodiment, the headset is physically connected to the processor or is remotely connected to the processor.

In one embodiment, a part of the bio-signal is pre-treated inside the hub (4) and is sent to the processor for being analyze. In one embodiment, the processor for interpreting/analyzing bio-signals measured by means of the electrodes (5) is localized in the hub (4), and is a chop for example Neurosky's chip or Emotiv's chip. In one embodiment, the processor is an external processor (i.e. the headset does not comprise the processor) for interpreting/analyzing bio-signal measured by the electrodes. According to one embodiment, the external processor is located for example in a smartphone, a computer, a server or the cloud.

According to one embodiment, said external processor is remotely connected to the headset, for example by means of a wireless transmitter and/or receiver. According to one embodiment, said external processor is physically connected to the headset, for example by means of a cable.

According to one embodiment, the external processor is a program or software such as Neuroscan, BioSemi, G-tech, Brain products or any equivalent software for monitoring an EEG signal. The processor may also include a software or a program for interpreting at least one bio-signal (for example an EEG, ECG) in order to correlate said at least one bio-signal with a particular mental state. According to one embodiment, the headset also comprises a memory for storing data related to the bio-signals.

According to one embodiment, the bio-signals detected by the electrodes (5) are fed through a sensor interface and digitalized to be stored for subsequent processing.

According to one embodiment, the memory configured for storing said bio-signals is located on the headset, preferably in the hub (4). According to one embodiment, the memory configured for storing said bio-signals is not located on the headset and data are sent to an external memory.

According to one embodiment, the headset further comprises a power supply or a battery. According to one embodiment, each electrode (5) is connected to an individual boarded battery. According to one embodiment, the power supply for the hub and/or each electrode (5) is symmetric or asymmetric.

In one embodiment, the wires/acquisition channels connected to each electrode (5) at one end form a network wherein every wires/acquisition channels are linking to a motherboard or a PCB enclosed in the hub (4). According to one embodiment, the at least 3 flexible branches (1, 2, 3) enclosed multi acquisition channels forming a network for connecting electrodes (5) to a PCB or a motherboard for data processing. According to one embodiment, the hub (4) comprises a printed circuit board (PCB). According to one embodiment, the hub (4) comprises the motherboard of the signal acquisition system i.e. the PCB holding a part of the electronic components of the system (e.g. an amplifier, a central processing unit (CPU), a memory) and provides connectors for other peripherals (e.g. the electrodes).

In one embodiment, the processor otherwise knew as a computer program, software or a computer control logic causes to perform desired functional step, for example detecting and classifying a type of mental state as for example monitoring and aid for diagnosis in medical applications. Mental states determined by such a processor can include emotion, desire, intention, concentration, attention, memory, relaxation, meditation etc. These mental states are composed by both healthy brain processes and also the pathological side of brain processes such as Alzheimer disease, attention deficit hyperactivity disorder, anxiety, insomnia, stress, etc. According to one embodiment, when a mental state is detected, a control signal is transmitted to an input/output interface for stimulating the subject with a neurofeedback, for example an auditory feedback.

According to one embodiment, the headset further comprises at least one earphone or earpiece. Said at least one earphone is used to impose an auditory stimuli for example an auditory neurofeedback. According to one embodiment, the earphone is a part of the headset. According to one other embodiment, the earphone is independent of the headset. According to one embodiment, the earphone is located on a flexible branch (1, 2, 3). According to one embodiment, the earphone is connected to the headset by means of a wire and configured for being inserted into the ear separately from the step of positioning the headset.

According to one embodiment, the headset further comprises a first earpiece and a second earpiece. According to one embodiment, the second branch (2) comprises the first earpiece and the third branch (3) comprises the second earpiece. According to one embodiment, each branch (2, 3) and its earpiece are connected with a metal piece that enables to control the height of earpiece relative to its branch. According to one embodiment, each branch (2, 3) and its earpiece are configured so that the earpiece is placed over a subject's ear when the audio headset is worn by a subject.

According to one embodiment, the first earpiece comprises the electrode of the second branch and the second earpiece comprises the electrode of the third branch.

According to one embodiment, the first earpiece and the second earpiece are circumaural earpieces; and the electrode of the second branch and the electrode of the third branch are positioned on their respective branches so that the electrodes rest against the skin disposed over the mastoid processes when the audio headset is worn by a subject. The mastoid processes are located behind the ears where the surface is plane, thereby giving robust results across various subjects. According to the Applicant, it is advantageous to position the electrodes against the mastoid processes and not directly against the ears due to the large morphological variability of ears.

According to one embodiment, the electrode of the second branch and the electrode of the third branch are textile electrodes, preferably fabric electrodes.

Therefore the invention also relates to an audio-headset for acquisition of a bio-signal from a subject, comprising:
a first earpiece;
a second earpiece;
an arch connecting the first earpiece and the second earpiece; said arch comprising a hub; wherein the arch, the first earpiece and the second earpiece are configured so that the earpieces are placed over a subject's ears when the audio headset is worn by a subject; and
at least one branch having a first end extending from the hub and a second free end (1b);
wherein
the at least one branch (1) comprises at least one electrode (5) configured for acquiring a bio-signal;
the at least one branch (1) comprises a concave surface with a radius of curvature, a collapsed state when the audio headset is not worn by a subject and an expanded state when the audio headset is worn by a subject.

According to one embodiment, as depicted in FIG. 11, the audio-headset (16) comprises an arch (15) a first earpiece (14) and a second earpiece (14), and at least one branch extending from the arch. As depicted in FIG. 11, the branch has a collapsed state (1') when not worn by a subject. According to one embodiment, as depicted in FIG. 12, the audio-headset (16) comprises an arch (15) a first earpiece (14) and a second earpiece (14), and at least two branches extending from the arch. As depicted in FIG. 12 for the purpose of illustration, one branch has an expanded state (1) and one branch has a collapsed state (1').

According to one embodiment, the at least one branch (1) extending from the hub, and thus from the arch, is a posterior branch or an anterior branch. According to one embodiment wherein the at least one branch is a posterior branch, the at least one electrode (5) is configured for acquiring a bio-signal at position P3 or P4 in the 10-10 system. According to one embodiment wherein the at least one branch is an anterior branch, the at least one electrode (5) is configured for acquiring a bio-signal at position AF3 or AF4 in the 10-10 system.

According to one embodiment, the radius of curvature in the collapsed state (CRc) and the radius of curvature in the expanded state (CRe) is such that:

$$CRc = \frac{CRe}{\Delta};$$

wherein $\Delta$ is equal to at least twice the standard deviation of the curvature radius of the scalp at a given position in the 10-10 system.

According to one embodiment, the radius of curvature at a given location on the scalp in the expanded state (CRe) is estimated using a 3 dimensional estimation of the local morphology of the scalp. Said method is called Morphological Overlapping Spheres (MOS).

According to one embodiment as depicted in FIGS. 13 and 14, the Morphological Overlapping Spheres method comprises the following steps:
MRI from a scalp is extracted, in particular T1 weighted MRI scalp tessellation is extracted;
EEG sensors positions are fitted on the scalp, for instance said positions are defined by standardized 10-10 international system (see the points in FIG. 13);
Spheres are estimated at each sensor location. Said spheres correspond to the estimation of a sphere that fits locally the shape of the scalp in the surroundings of each sensor and passing through the contact point of the hub;
L and CRe are computed thanks to the estimated spheres. CRe is the average radius of the spheres over the population and L is the geodesic distance between the sensor and the contact point of the hub.

Said estimation provides two parameters L and CRe, namely the length of the branch extending from the hub and the curvature radius of the branch.

The Morphological Overlapping Spheres method is applied to more than 152 human MRI all over the scalp positions so that relevant statistical data may be computed.

In particular standard deviation 6 may be computed. From said standard deviation 6, a parameter $\Delta$ may be obtained such that $\Delta > 2\sigma$. The CRe estimations follow a Gaussian distribution, 2 $\sigma$ were chosen to be based on a Confidence Interval of 95% over the tested population.

The said method may be used for any position within the 10-10 system.

Anterior Branch

In an exemplary embodiment, for an anterior branch, especially for a branch having an electrode configured for acquiring a bio-signal at position AF3 or AF4 in the 10-10 system, the curvature radius in the expanded state is 9.21 cm.

The standard deviation is 1.05 cm.

Thus, in said embodiment, the ratio between the radius of curvature in the expanded state (CRe) and the radius of curvature in the collapsed state (CRc) is higher than 2.10.

Posterior Branch

In an exemplary embodiment, for an anterior branch, especially for a branch having an electrode configured for acquiring a bio-signal at position P3 or P4 in the 10-10 system, the curvature radius in the expanded state is 8.80 cm.

The standard deviation is 1.18 cm.

Thus, in said embodiment, the ratio between the radius of curvature in the expanded state (CRe) and the radius of curvature in the collapsed state (CRc) is higher than 2.36.

According to the Applicant, said ratio between the expanded state and the collapsed state ensure suitable positioning of the electrodes. It is particularly useful for bringing into optimal direct contact said electrodes with the scalp, even when hair exits on the scalp.

According to one embodiment, the at least one electrode (5) of the at least one posterior branch or the at least one anterior branch comprises at least two pins (6) having a first free end comprising a skin contact interface (8) and a second end connected to at least one flexure element (7).

Said electrodes with independent pins enable suitable contact of each pin independently of the scalp morphology. According to the Applicant the electrodes with pins used with the headset of the invention ensure an optimal positioning of the electrodes both at a macroscale and at a local scale.

According to one embodiment, the first earpiece and the second earpiece comprise each at least one textile electrode (5), the earpieces and the arch being configured such that the textile electrodes (5) rest against the skin disposed over the mastoid processes when the audio-headset is worn by a subject.

According to the Applicant, the mastoid process is a sensitive area wherein electrodes with pin may be unpleasant to the subject. The use of textile electrodes ensures comfort to the subject.

According to one embodiment, the audio-headset comprises at least two posterior branches (1r, 1l) each having a first end extending from the hub (4) and a second free end; each posterior branch comprising at least one electrode (5) configured for acquiring a bio-signal, preferably the first posterior branch is configured for acquiring a bio-signal at position P3 in the 10-10 system and the second posterior branch is configured for acquiring a bio-signal at position P4 in the 10-10 system; wherein the at least two posterior branches (1r, 1l) comprise a concave surface with a radius of curvature, a collapsed state and an expanded state; wherein the ratio between the radius of curvature in the expanded state (CRe) and the radius of curvature in the collapsed state (CRc) is higher than 2.36.

According to one embodiment, the audio-headset comprises at least two anterior branches (1r, 1l) each having a first end extending from the hub (4) and a second free end; each anterior branches comprising at least one electrode (5) configured for acquiring a bio-signal, preferably the first anterior branch is configured for acquiring a bio-signal at position AF3 in the 10-10 system and the second anterior branch is configured for acquiring a bio-signal at position AF4 in the 10-10 system; wherein the at least two anterior branches (1r, 1l) comprise a concave surface with a radius of curvature, a collapsed state and an expanded state; wherein the ratio between the radius of curvature in the expanded state (CRe) and the radius of curvature in the collapsed state (CRc) is higher than 2.10.

According to one embodiment, the headset comprises at least one anterior branch connected to the arch and at least one posterior branch connected to the arch.

According to one embodiment, the at least one posterior branch or the at least one anterior branch is releasably connected to the hub. Thus the headset may be used in 2 modes:
  Recording mode, with the branches plugged; and
  Nomad mode, with the branches unplugged.

According to one embodiment, the first earpiece and the second earpiece are circumaural earpieces.

According to one embodiment, the at least one electrode (5) of the first earpiece and the at least one electrode (5) of the second earpieces are fabric electrodes. According to one embodiment, the at least one electrode (5) of the first earpiece and the at least one electrode (5) of the second earpieces comprises an argent coated textile, preferably an argent coated polyester textile.

According to one embodiment, the at least one electrode (5) of the first earpiece and the at least one electrode (5) of the second earpieces comprise a plurality of contact surfaces. Especially as depicted in FIG. 17 the textile electrode comprises a common part (51) from which extends a plurality of strips (52); said strips being independent. According to one embodiment, as depicted in FIG. 18, when the earpiece (14) comprises an electrode, the common part (51) is embedded within the earpiece and at least part of the strips (52) are located on the outer surface of the earpiece. Preferably, the strips (52) are sewed to the outer surface of the earpiece (14).

According to one embodiment, the at least one posterior branch or the at least one anterior branch comprises an amagnetic metal sheet in order to avoid EEG perturbation. According to one embodiment, the amagnetic metal sheet is at least 0.5 mm thick. According to one embodiment, the amagnetic metal sheet is stamped or molded. According to one embodiment, a rubber part or a foam is connected to the amagnetic metal sheet. According to one embodiment, said rubber part or foam is in contact with the subject's head when the headset is worn to ensure comfort to the subject. According to one embodiment, the foam is thermoformed. According to one embodiment, the foam is made of polyethylene or polyamide. According to one embodiment, the electrodes are located in a casing molded in the foam or the rubber part. According to one embodiment, the at least one posterior branch or the at least one anterior branch is made of acrylonitrile butadiene styrene. According to one embodiment, the at least one posterior branch or the at least one anterior branch is made of polyamide.

According to one embodiment, the at least 3 electrodes of the audio-headset comprise a ground electrode, a reference electrode, and at least one acquisition electrode.

According to one embodiment, the at least 3 electrodes (5) of the audio-headset are configured to carry out an electroencephalography (EEG), and/or optionally electromyography (EMG), electrooculography (EOG) or electrocardiography (ECG).

According to one embodiment, the audio-headset is further connected to a bio-signal processor for analyzing and interpreting the measured bio-signal.

According to one embodiment, the audio-headset comprises an electronic circuit (13) for acquiring a bio-signal comprising an amplifier, an A/D converter and a signal filter.

According to one embodiment, the audio-headset comprises a wireless transmitter and/or receiver.

The present invention also relates to a method of providing neurofeedback to at least one subject, the method comprising the following steps:
  placing on the top of the head of a subject an audio-headset for bio-signal acquisition according to the present invention;
  acquiring a bio-signal using the headset;
  analyzing the bio-signal; and
  providing an audio-feedback to said subject in accordance with the measured bio-signal.

According to one embodiment, the method further comprises the step of providing a further feedback such as a tactile, visual or auditory feedback.

According to one embodiment, the analysis of the bio-signal comprises correlating the bio-signal with a specific mental state and providing the subject with a feedback comprising at least one suggestion for improving the subject mental state According to one embodiment, the headset is not an audio headset. In said embodiment, the headset comprises a hub; at least 3 flexible branches, each branch having a first end extending from the hub and a second free end, and at least 3 electrodes, wherein at least one electrode is located on each of the at least 3 flexible branches, said electrodes being configured for acquiring a bio-signal; wherein at least one branch comprises a concave surface with a radius of curvature, a collapsed state when the headset is not worn by a subject and an expanded state when the headset is worn by a use, wherein the at least one electrode (5) of the said branch comprises at least two pins having a first free end comprising a skin-contact interface (8) and a second end connected to at least one flexure element; and wherein the two others branches comprise each at least one textile electrode (5), each of said two branches being configured such that the textile electrodes (5) rest against the skin disposed over the mastoid processes when the headset is worn by a subject.

According to one embodiment, the headset further comprises a wireless transmitter and/or receiver. In one embodiment, the wireless transmitter and/or receiver is located on the hub (4), on its external surface. Advantageously, said wireless transmitter and/or receiver is configured for sending outputs to an external processor. According to one other embodiment, the wireless transmitter and/or receiver is also configured for receiving inputs from a computer program, software or any processor able to generate neurofeedbacks or instructions for the headset. For example, the wireless transmitter and/or receiver is a Wi-Fi, a Bluetooth or XBee transmitter/receiver. In some embodiment, the headset is remotely connected to a computer for analyzing bio-signals. In some embodiment, the wireless transmitter and/or receiver is configured to receive digitized output from an A/D converter and to transmit the digitized data to an external device for example a computer, a tablet or a smart-phone. According to one embodiment, the data are digitized inside the hub (4). According to one embodiment, the data are digitized inside the at least three electrodes (5).

According to one embodiment, the headset is configured for monitoring brainwaves to achieve a desired mental state. Advantageously, the devices and methods may be portable for a suitable use in any environment and location where the subject's mental state may be enhanced or monitored.

In some embodiment, the headset is configured for receiving EEG data from the subject, analyzing the EEG data, correlating it with a specific mental state; and providing the subject with feedback comprising at least one suggestion for improving the subject mental state. In one embodiment, a suggestion for improving a mental state is a neurofeedback, for example an auditory feedback such as music. According to one embodiment, the audio-feedback is provided by the earphone.

In an exemplary embodiment, the headset is used for providing a neurofeedback wherein, at the beginning, a dataset is used for calibration purposes composed by the following steps:
  recording bio-signal data using one thread;
  computing in another thread the calibration parameter that will be used during the current session i.e. computing the signal quality, artifacts detection and individual spectral features for example by updating previous calibration features;
  starting a neurofeedback session in another thread.

According to one embodiment, the neurofeedback session computes the relaxation level of the subject by mixing two bio-signals for example heart beat frequency and brain signal frequency and spatial features such as alpha or beta rhythm recorded at several scalp locations such as P3, P4 or Pz. In a further embodiment, the neurofeedback session also comprises the step of computing statistics based on the anti-correlation of said two bio-signals. In a preferred embodiment, the neurofeedback is an audio feedback, wherein music is composed by a low frequency impact of the gauge and a background sound designed music.

REFERENCES

1—Acquisition flexible branch (in the expanded state)
1'—Acquisition flexible branch (in the collapsed state)
1r—Right acquisition flexible branch
1l—Left acquisition flexible branch
1a—First end of the acquisition flexible branch
1b—Free end of the acquisition flexible branch
1l—Anterior flexible branch
11r—Right anterior flexible branch
11l—Left anterior flexible branch
12—Posterior flexible branch
12r—Right posterior flexible branch
12l—Left posterior flexible branch
2—Left peripheral branch (in the expanded state)
2'—Left peripheral branch (in the collapsed state)
2a—First end of the left peripheral branch
2b—Free end of the left peripheral branch
3—Right peripheral branch
3a—First end of the right peripheral branch
3b—Free end of the right peripheral branch
4—Hub
5—Electrodes
51—Common part of a textile electrode
52—Strips of a textile electrode
53—Connecting cable connecting the textile electrode to the PCB
6—Pins
7—Flexure element
8—Skin contact interface
9—Circuit contact interface
10—Matrix setting
13—Electronic circuit
14—Earpiece
15—Arch
16—Audio-headset
17—Flexible blade
α, β—Load angles

EXAMPLES

The present invention is further illustrated by the following example.

Example 1

Figure 1:
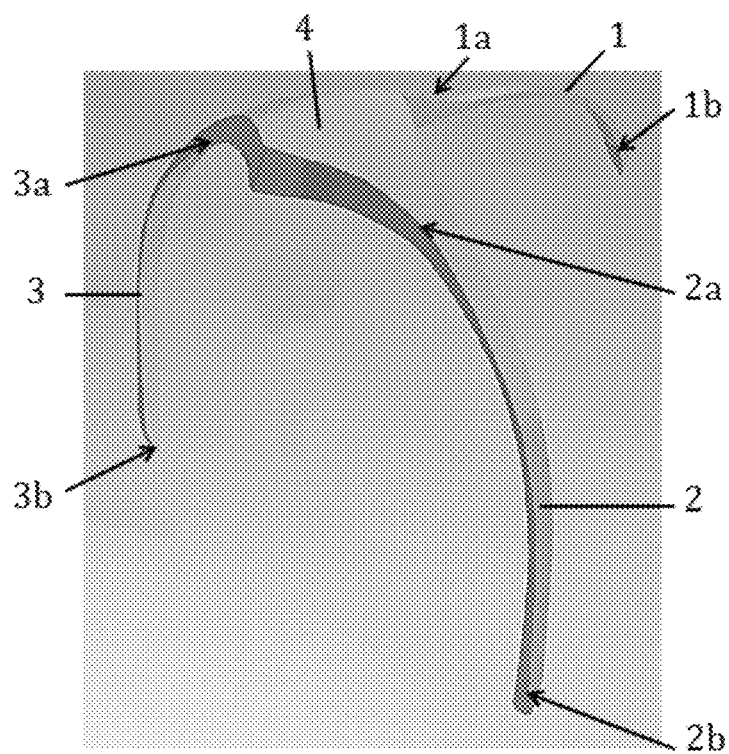
FIG. 1 is a schematic representation of a headset comprising at least 3 flexible branches (1, 2, 3) in an expanded configuration.
Figure 2:
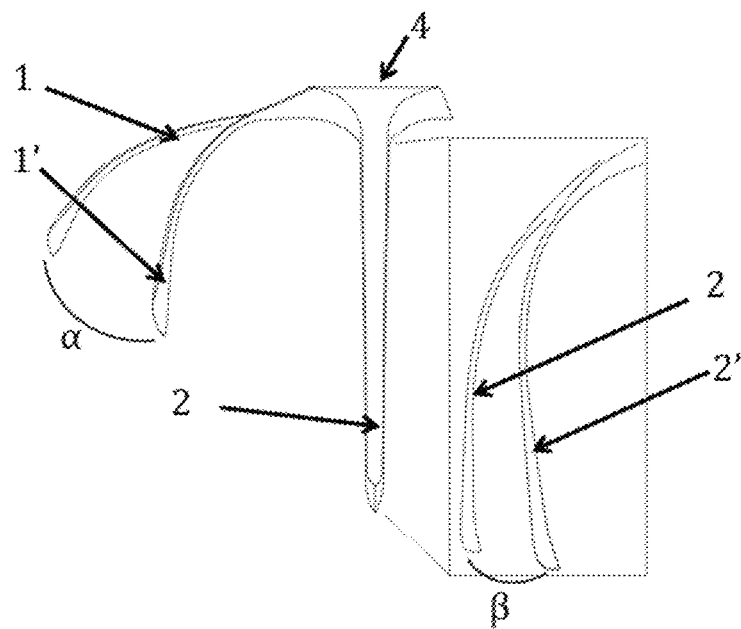
FIG. 2 is a schematic representation of a headset comprising at least 3 flexible branches (1, 2, 3) in a collapsed configuration and an expanded configuration.
Figure 3:
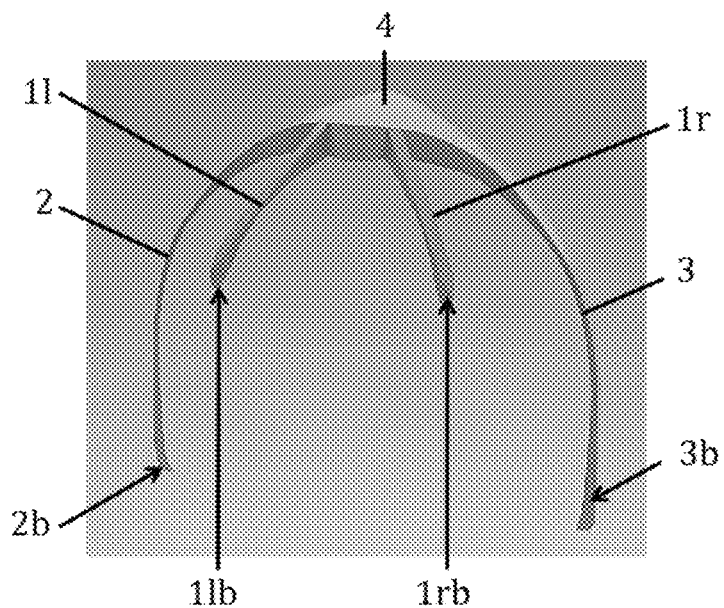
FIG. 3 is a schematic representation of a headset with 4 flexible branches (1r, 1l, 2, 3) for bio-signal acquisition in an expanded configuration.
Figure 4:
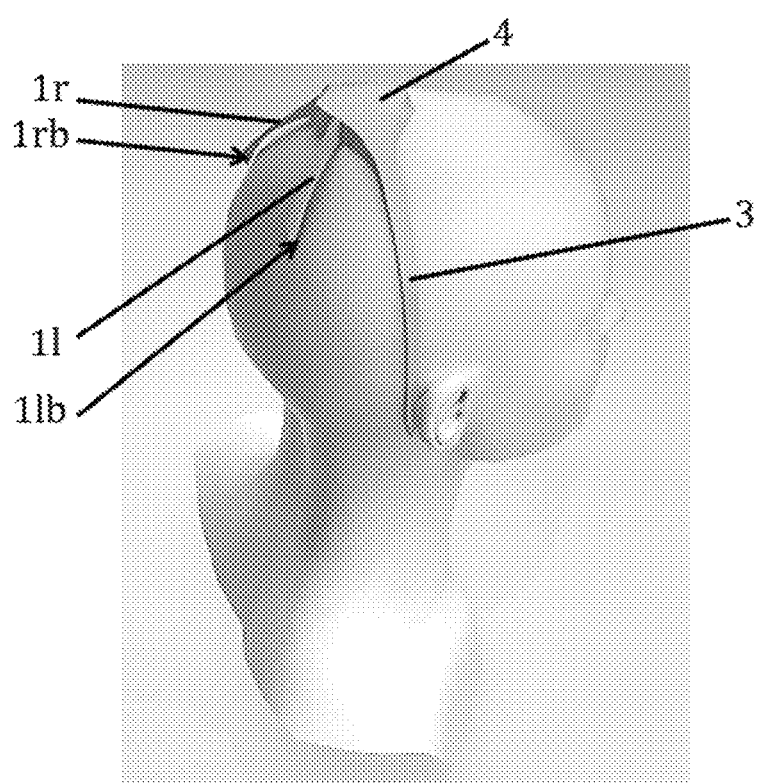
FIG. 4 is a schematic representation of a headset with 4 flexible branches (1r, 1l, 2, 3) for bio-signal acquisition in situ, positioned on a head in an expanded configuration.
Figure 5:
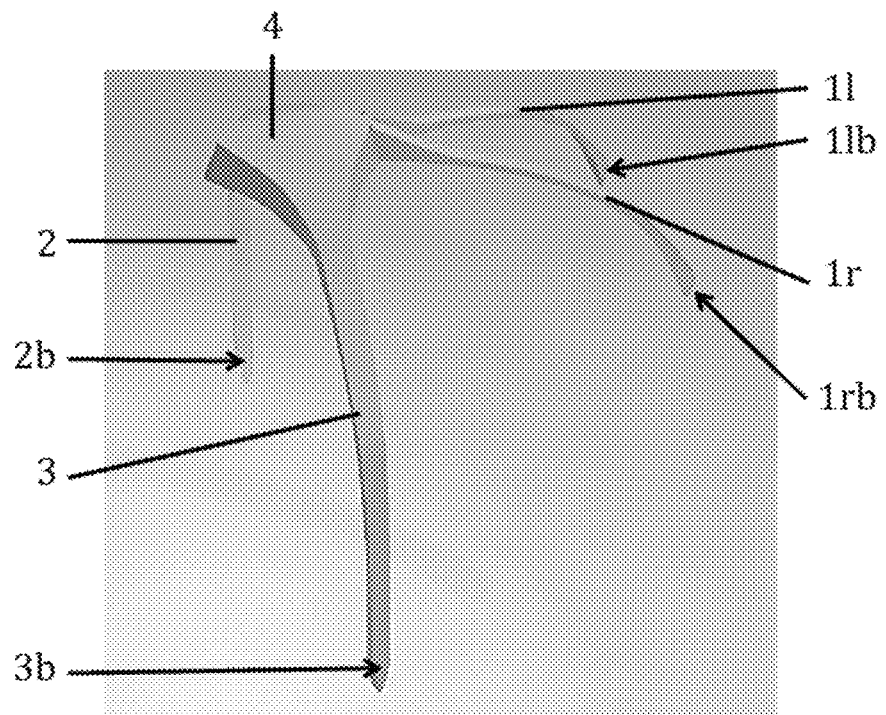
FIG. 5 is a schematic representation of the headset with 4 flexible branches (1r, 1l, 2, 3) for bio-signal acquisition in an expanded configuration.
Figure 6:
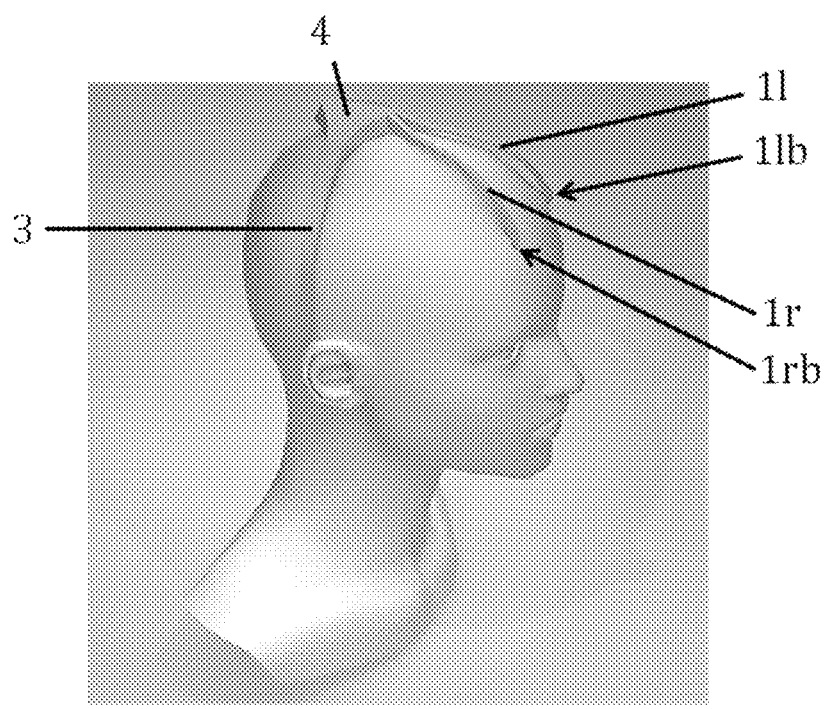
FIG. 6 is a schematic representation of the headset with 4 flexible branches (1r, 1l, 2, 3) for bio-signal acquisition in situ, positioned on a head in an expanded configuration.
Figure 7:
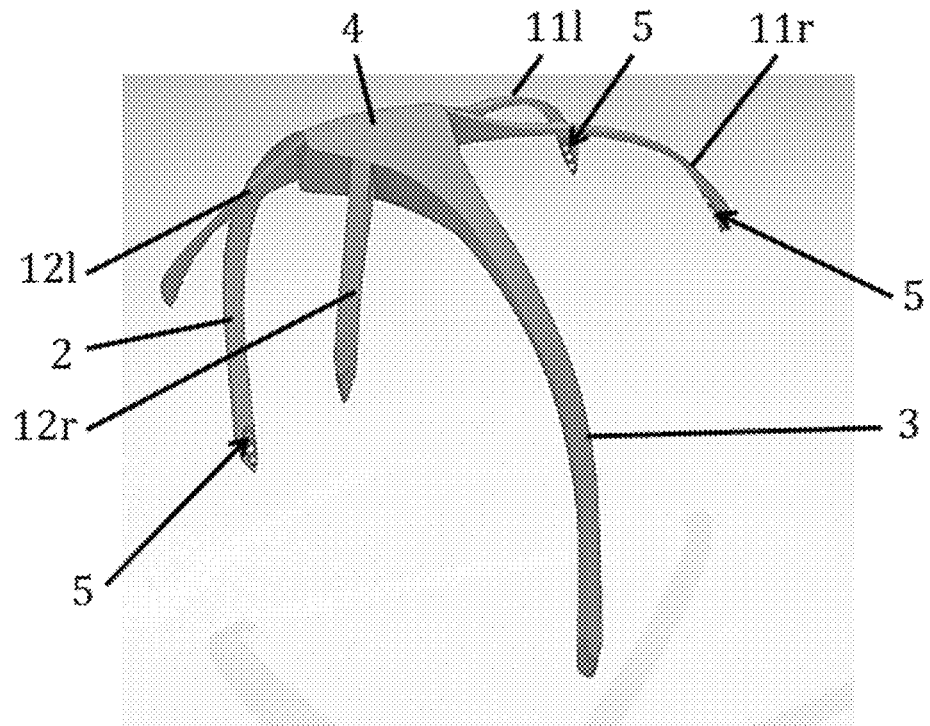
FIG. 7 is a schematic representation of the headset with 6 flexible branches for bio-signal acquisition in an expanded configuration.
Figure 8:
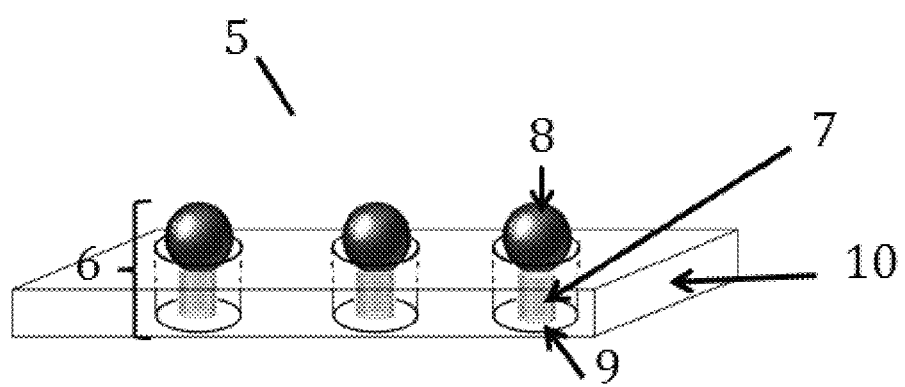
FIG. 8 is a schematic representation of an electrode (5) comprising spring loaded pins (6) plunged on a matrix setting (10).
Figure 9:
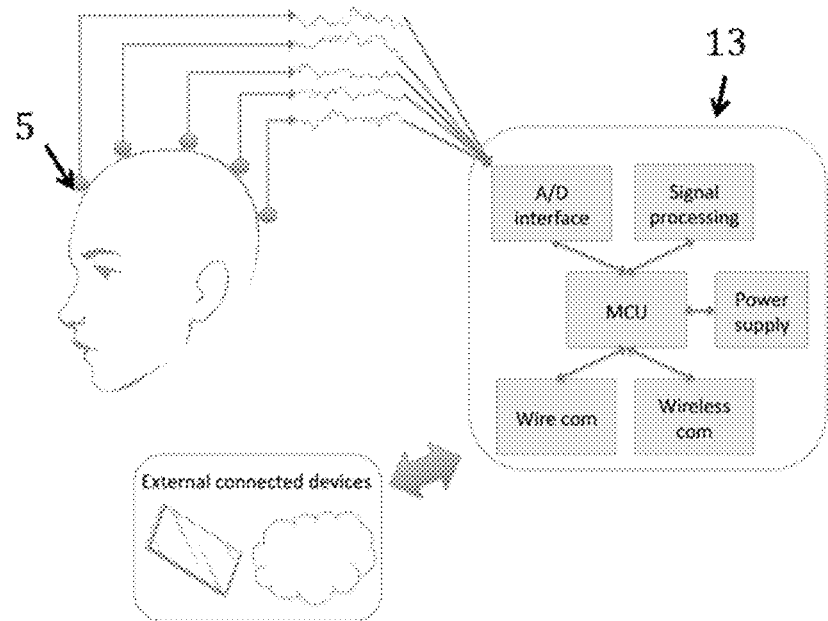
FIG. 9 is a schematic representation of the electronic devices integrated in the headset.
Figure 10:
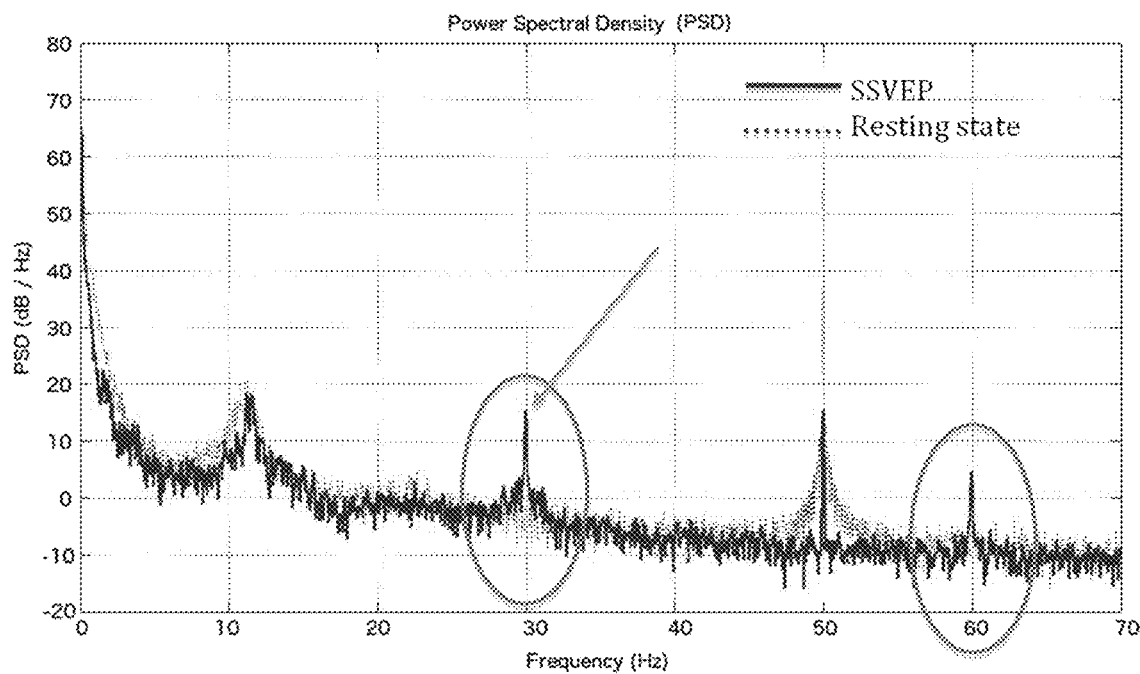
FIG. 10 is a graph representing the evolution of the PSD (Power Spectral Density—Decibel/Hertz) according to the frequency (Hz).
Figure 11:
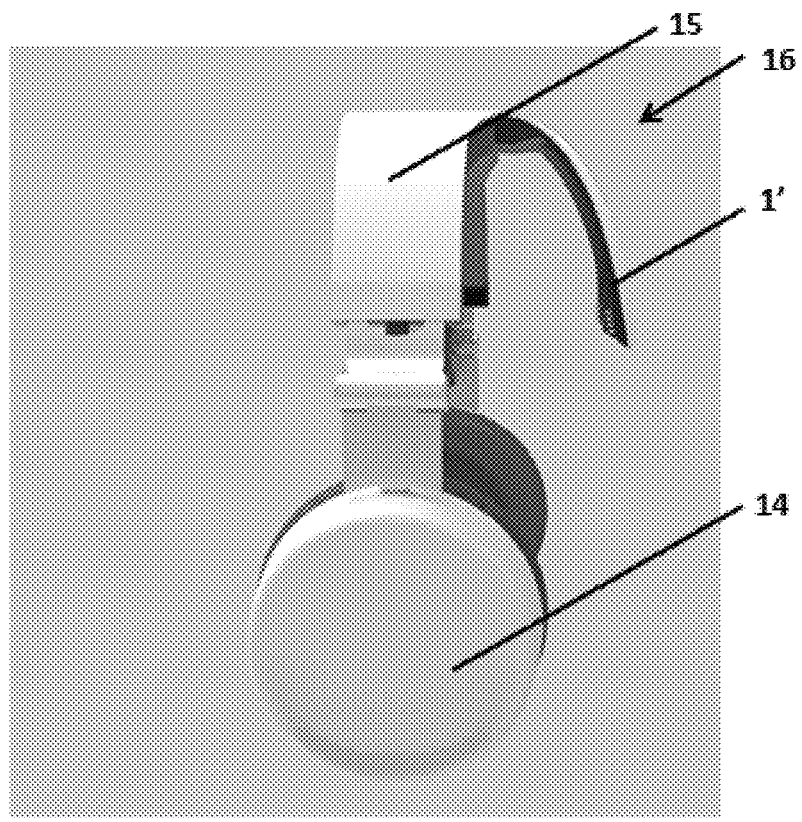
FIG. 11 is a schematic representation of an audio-headset according to one embodiment of the invention in the collapsed configuration.
Figure 12:
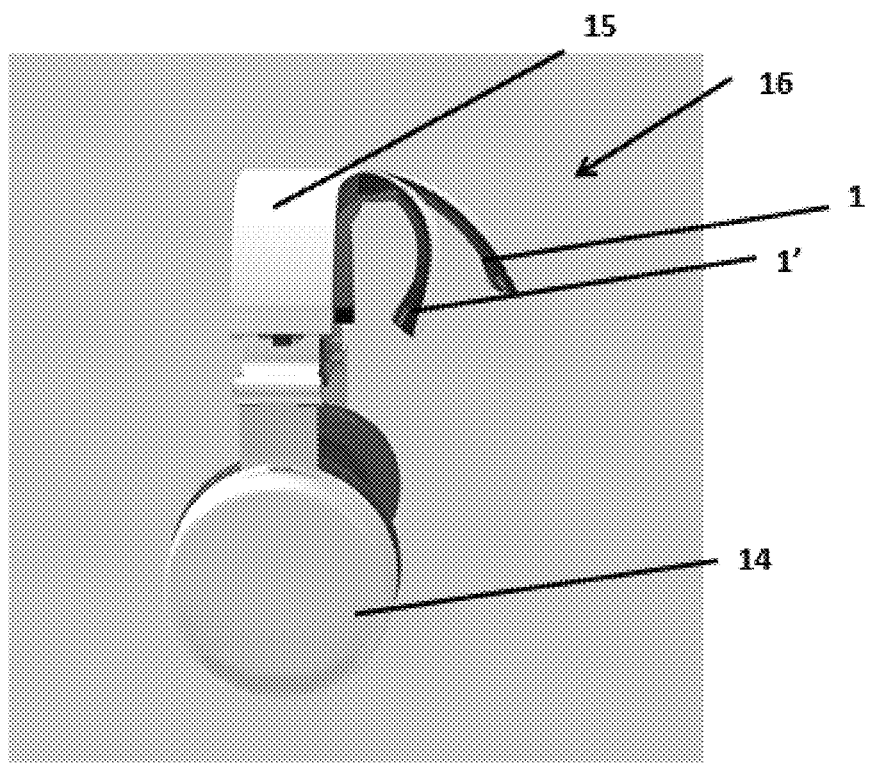
FIG. 12 is a schematic representation of an audio-headset with, for the purpose of illustration, one posterior branch in the expanded configuration (1) and one posterior branch is the collapsed configuration (1').
Figure 13:
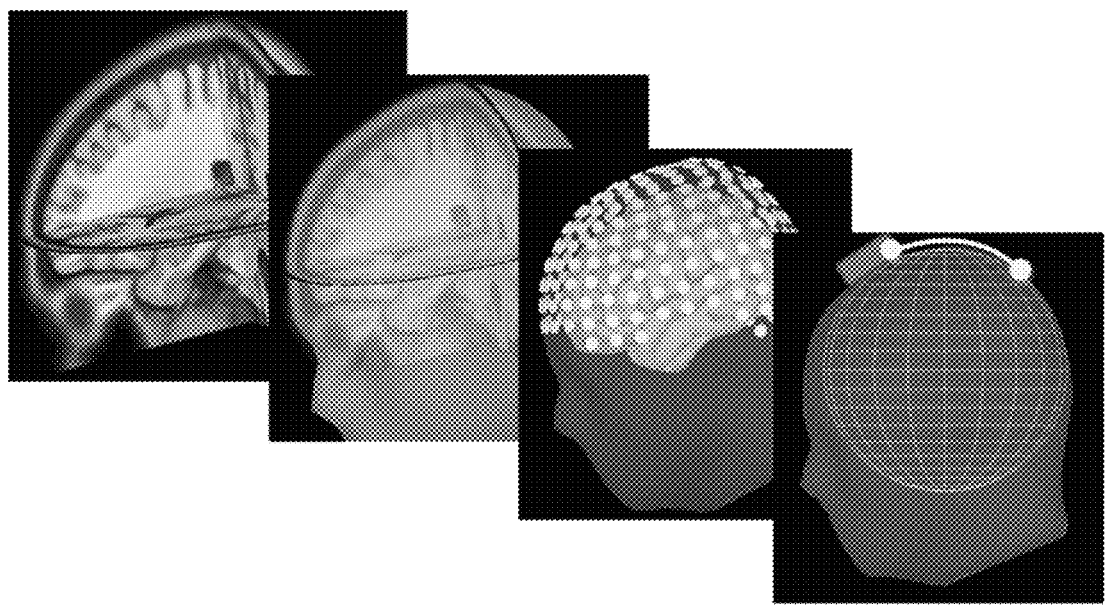
FIG. 13 is a schematic illustration of the Morphological Overlapping Spheres (MOS) method.
Figure 14:
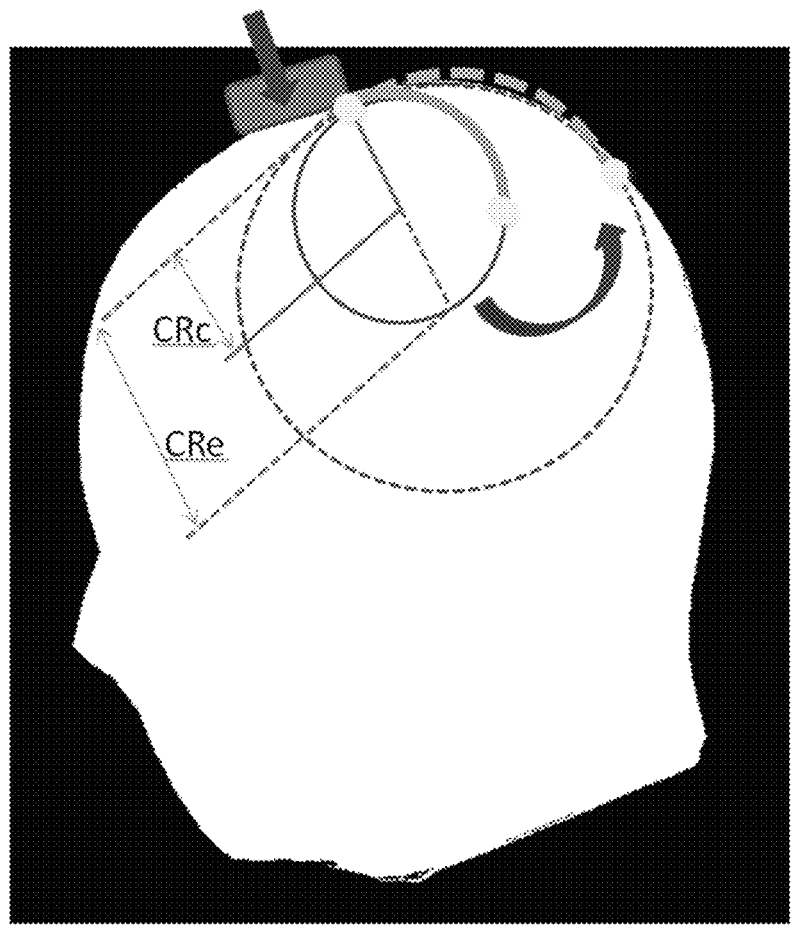
FIG. 14 is a schematic representation of the radius of curvature of a branch in a collapsed state (CRc) and in an expanded state (CRe). The rectangle illustrates the hub (4). The point in contact with the hub illustrates the first end of the branch. Fill (respectively dot) line illustrates the branch at the collapsed configuration (respectively expanded configuration). The points at the free end of each branch represent the electrodes positioning. Circles are the sections of the spheres defining the curvature radius of each branch. The arrow on the hub displays the movement the subject is applying to position the headset and thus the extension of the branch from the collapsed configuration to the expanded configuration.
Figure 15:
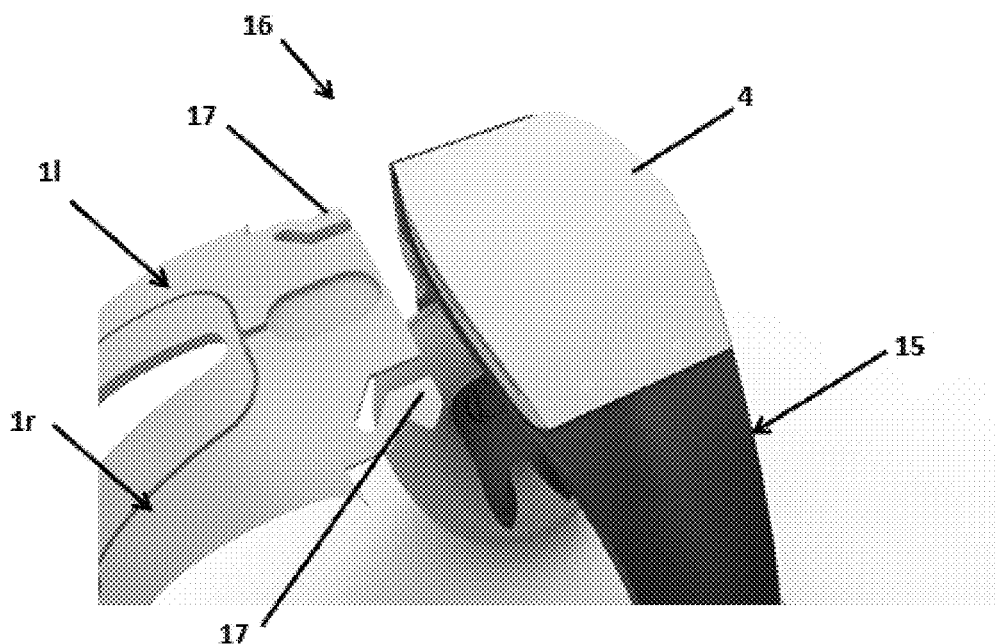
FIG. 15 illustrates the connection between the hub and the branch of the audio-headset of the invention.

This example shows the results of Steady State Visually Evoked Potentials (SSVEP).
EEG bio-signals were recorded during visual stimulations at the scalp location Oz using the headset according to the present invention. The visual stimulation was composed by chessboard flashing at the specific frequency of 30 Hz. A recording session at rest was also done in order to compare the results at the same location without visual stimulations. FIG. 10 shows the Power Spectral Density (PSD) of one minute recording. We can see that the PSD increases at 30 Hz (and also its harmonic at 60 Hz) directly related to the SSVEP. From our analysis, the peak amplitude at 30 Hz reaches twice time the PSD level at 30 Hz in resting state condition using only 3s of buffer acquisition. This ratio reaches five times using 15s of buffer acquisition and ten times using one minute of buffer acquisition.

Example 2

Figure 16:
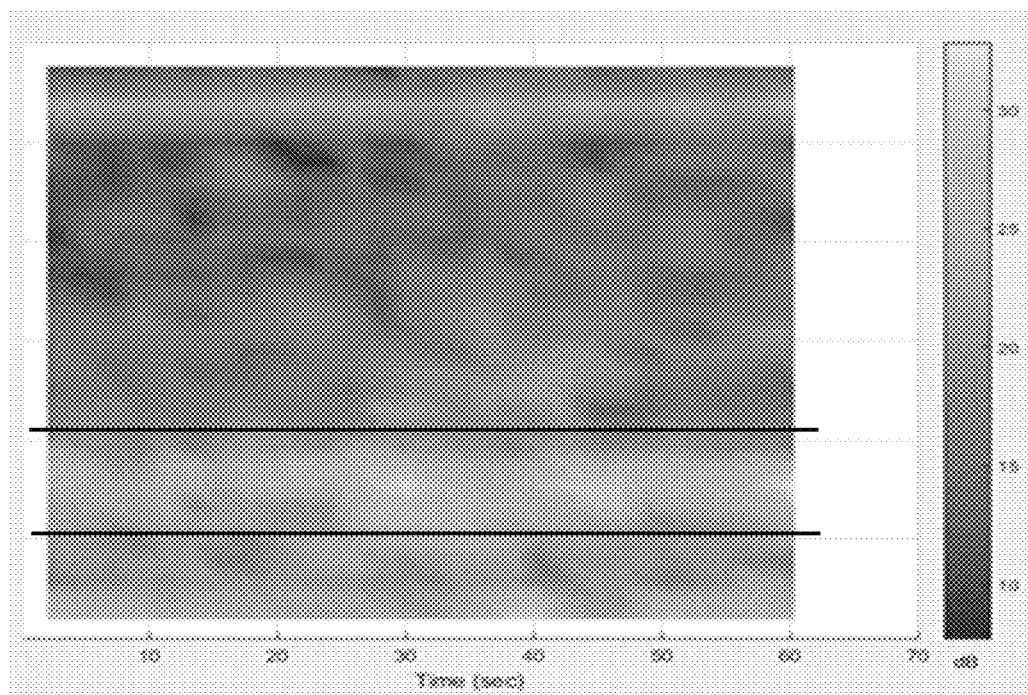
FIG. 16 illustrates an EEG time frequency map for EO-EC showing alpha blocking detection; the signal has been recorded with textile electrodes.
Figure 17:
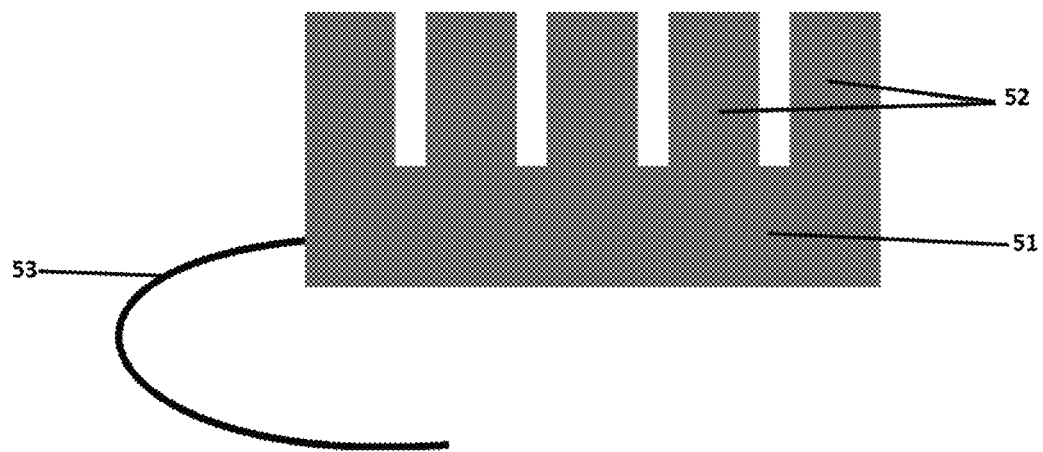
FIG. 17 illustrates a textile electrode according to one embodiment of the invention.
Figure 18:
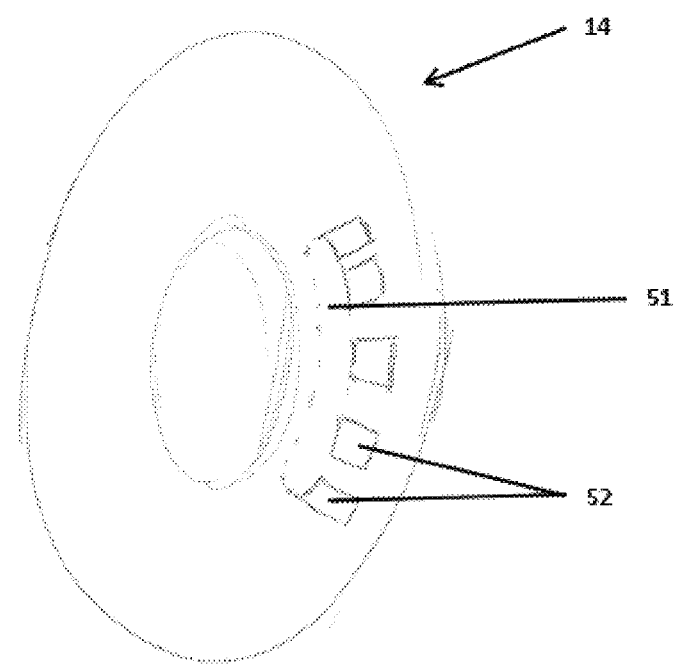
FIG. 18 illustrates an earpiece comprising a textile electrode according to one embodiment of the invention.

FIG. 16 illustrates a time-frequency map (computation based on Morlet wavelet) of an EEG recording during an eyes closed condition. It is well known from the very beginning of EEG that eyes closed condition versus eyes opened condition shows "alpha blocking". This figure displays on x-axis the time of recording and the PSD on y-axis. We can see clearly strong alpha (8-12 Hz) power increasing all over the recording.

The invention claimed is:

1. An audio-headset for acquisition of a bio-signal from a subject, comprising:
a first earpiece and a second earpiece;
an arch connecting the first earpiece and the second earpiece, said arch comprising a hub,
wherein the arch, the first earpiece and the second earpiece are configured so that the earpieces are placed over a subject's ears when the audio headset is worn by the subject; and
at least one posterior branch having a first end extending from the hub and a second free end, wherein,
the at least one posterior branch comprises at least one electrode configured for acquiring a bio-signal,
the at least one posterior branch comprises a concave surface with a radius of curvature, a collapsed state when the audio headset is not worn by the subject and an expanded state when the audio headset is worn by the subject;
wherein the ratio between the radius of curvature in the expanded state and the radius of curvature in the collapsed state is higher than 2.36, and
the at least one electrode of the at least one posterior branch comprises at least two pins, each pin having a first free end comprising a skin-contact interface and a second end connected to at least one flexure element, and
the first earpiece and the second earpiece comprise each at least one textile electrode, the earpieces and the arch being configured such that the textile electrodes rest against the skin disposed over the mastoid processes when the audio-headset is worn by the subject.

2. The audio-headset according to claim 1, wherein the at least one posterior branch comprises at least one electrode configured for acquiring a bio-signal at position P3 or P4 in a 10-10 system.

3. The audio-headset according to claim 1, wherein the audio-headset comprises at least two posterior branches.

4. The audio-headset according to claim 3, wherein the first posterior branch is configured for acquiring a bio-signal at position P3 in a 10-10 system and the second posterior branch is configured for acquiring a bio-signal at position P4 in the 10-10 system.

5. The audio-headset according to claim 1, wherein the at least one posterior branch is releasably connected to the hub.

6. The audio-headset according to claim 1, wherein the first earpiece and the second earpiece are circumaural earpieces.

7. The audio-headset according to claim 1, wherein the at least one electrode of the first earpiece and the at least one electrode of the second earpieces are fabric electrodes.

8. The audio-headset according to claim 1, wherein the at least one electrode of the first earpiece and the at least one electrode of the second earpieces comprises an argent coated textile.

9. The audio-headset according to claim 1, wherein the at least one electrode of the first earpiece and the at least one electrode of the second earpieces comprise a plurality of contact surfaces.

10. The audio-headset according to claim 1, the at least one electrode of the first earpiece and the at least one electrode of the second earpieces comprise a common part from which extends a plurality of strips; and wherein the common part is embedded within the earpiece and at least part of the strips are located on the outer surface of the earpiece.

11. The audio-headset according to claim 1, wherein the at least one posterior branch comprises an amagnetic metal sheet.

12. The audio-headset according to claim 1, wherein the electrodes of the audio-headset comprise a ground electrode, a reference electrode, and at least one acquisition electrode.

13. The audio-headset according to claim 1, wherein the electrodes of the audio-headset are configured to carry out an electroencephalography, and/or electromyography, electrooculography or electrocardiography.

14. The audio-headset according to claim 1, being further connected to a bio-signal processor for analyzing and interpreting the measured bio-signal.

15. An audio-headset for acquisition of a bio-signal from a subject, comprising:
    a first earpiece;
    a second earpiece;
    an arch connecting the first earpiece and the second earpiece, said arch comprising a hub,
    wherein the arch, the first earpiece and the second earpiece are configured so that the earpieces are placed over a subject's ears when the audio headset is worn by the subject; and
    at least one anterior branch having a first end extending from the hub and a second free end, wherein,
    the at least one anterior branch comprises at least one electrode configured for acquiring a bio-signal,
    the at least one anterior branch comprises a concave surface with a radius of curvature, a collapsed state when the audio headset is not worn by the subject and an expanded state when the audio headset is worn by the subject;
    wherein the ratio between the radius of curvature in the expanded state and the radius of curvature in the collapsed state is higher than 2.10, and
    the at least one electrode of the at least one anterior branch comprises at least two pins, each pin having a first free end comprising a skin-contact interface and a second end connected to at least one flexure element, and
    the first earpiece and the second earpiece comprise each at least one textile electrode, the earpieces and the arch being configured such that the textile electrodes rest against the skin disposed over the mastoid processes when the audio-headset is worn by the subject.

16. The audio-headset according to claim 15, wherein the at least one anterior branch comprises at least one electrode configured for acquiring a bio-signal at position AF3 or AF4 in a 10-10 system.

17. The audio-headset according to claim 15, comprising at least two anterior branches wherein the electrodes comprised in the two anterior branches are disposed so that the first anterior branch is configured for acquiring a bio-signal at position AF3 in a 10-10 system and the second anterior branch is configured for acquiring a bio-signal at position AF4 in the 10-10 system.

18. The audio-headset according to anyone of claim 15, wherein the at least one anterior branch is releasably connected to the hub.

19. A method for providing neurofeedback to at least one subject, the method comprising the following steps:
    placing on the top of the head of a subject an audio-headset for bio-signal acquisition, the headset comprising:
    a first earpiece and a second earpiece;
    an arch connecting the first earpiece and the second earpiece, said arch comprising a hub,
    wherein the arch, the first earpiece and the second earpiece are configured so that the earpieces are placed over a subject's ears when the audio headset is worn by the subject; and
    at least one posterior branch having a first end extending from the hub and a second free end, wherein,
    the at least one posterior branch comprises at least one electrode configured for acquiring a bio-signal,
    the at least one posterior branch comprises a concave surface with a radius of curvature, a collapsed state when the audio headset is not worn by the subject and an expanded state when the audio headset is worn by the subject; wherein the ratio between the radius of curvature in the expanded state and the radius of curvature in the collapsed state is higher than 2.36, and
    the at least one electrode of the at least one posterior branch comprises at least two pins, each pin having a first free end comprising a skin-contact interface and a second end connected to at least one flexure element, and
    the first earpiece and the second earpiece comprise each at least one textile electrode, the earpieces and the arch being configured such that the textile electrodes rest against the skin disposed over the mastoid processes when the audio-headset is worn by the subject;
    acquiring a bio-signal using the headset;
    analyzing the acquired bio-signal; and
    providing an audio-feedback to said subject in accordance with the measured bio-signal.

20. The method for providing neurofeedback according to claim 19, wherein the analysis of the bio-signal comprises the step of correlating the bio-signal with a specific mental state and providing the subject with a feedback comprising at least one suggestion for improving the subject mental state.

* * * * *